United States Patent
Rozema et al.

(10) Patent No.: US 9,011,919 B2
(45) Date of Patent: *Apr. 21, 2015

(54) COMPOSITIONS FOR TARGETED DELIVERY OF SIRNA

(75) Inventors: David B. Rozema, Middleton, WI (US); David L. Lewis, Madison, WI (US); Darren H. Wakefield, Fitchburg, WI (US); Torsten Hoffmann, Weil am Rhein (DE); Eric Kitas, Baselland (CH); Peter Mohr, Basel (CH); Philipp Hadwiger, Kulmbach (DE); Wilma Thuer, Kulmbach (DE); Linda Valis, Bamberg (DE)

(73) Assignee: Arrowhead Madison Inc., Madison, WI (US)

( * ) Notice: Subject to any disclaimer, the term of this patent is extended or adjusted under 35 U.S.C. 154(b) by 216 days.

This patent is subject to a terminal disclaimer.

(21) Appl. No.: 13/615,938

(22) Filed: Sep. 14, 2012

(65) Prior Publication Data

US 2013/0245091 A1    Sep. 19, 2013

Related U.S. Application Data

(62) Division of application No. 13/032,029, filed on Feb. 22, 2011, now Pat. No. 8,313,772.

(60) Provisional application No. 61/307,490, filed on Feb. 24, 2010.

(51) Int. Cl.
| | |
|---|---|
| *A61K 9/14* | (2006.01) |
| *C07H 21/02* | (2006.01) |
| *C07K 1/00* | (2006.01) |
| *A61K 47/32* | (2006.01) |
| *A61K 9/08* | (2006.01) |
| *A61K 48/00* | (2006.01) |
| *C12N 15/11* | (2006.01) |
| *C12N 15/87* | (2006.01) |
| *A61K 47/48* | (2006.01) |

(52) U.S. Cl.
CPC . *A61K 47/32* (2013.01); *A61K 9/08* (2013.01); *A61K 48/0041* (2013.01); *C12N 15/111* (2013.01); *C12N 15/87* (2013.01); *C12N 2310/14* (2013.01); *C12N 2320/32* (2013.01); *A61K 47/48169* (2013.01); *A61K 47/48092* (2013.01)

(58) Field of Classification Search
USPC .................. 424/486; 536/24.5; 530/333, 345
See application file for complete search history.

(56) References Cited

U.S. PATENT DOCUMENTS

| | | | |
|---|---|---|---|
| 2008/0152661 A1 | 6/2008 | Rozema et al. | |
| 2008/0281041 A1 | 11/2008 | Rozema et al. | |

FOREIGN PATENT DOCUMENTS

| | | |
|---|---|---|
| JP | 2007-112768 A | 10/2007 |
| WO | WO 2008022309 A2 | 2/2008 |

OTHER PUBLICATIONS

Ayelet, D. et al.,'Enhanced biorecognition and internalization of HPMA copolymers containing multiple or multivalent carbohydrate side-chains by human hepatocarcinoma cells', Bioconjugate Chemistry, 2001, vol. 12, pp. 890-899.
Frish, B. et al.,'A new triantennary galactose-targeted PEGylated gene carrier, characterization of its complex with DNA, and transfection of hepatoma cells', Bioconjugate Chemistry, 2004, vol. 15, pp. 754-764.
Lee, Y.C.,'Binding modes of mammalian hepatic Gai/GaiNC receptors', Ciba Foundation Symposium, 1989, vol. 145, pp. 80-95.
Li, Y. et al.,'Targeted delivery of macromolecular drugs: asialoglycoprotein receptor (ASGPR) expression by selected hepatoma cell lines used in antiviral drug development', Current Drug Delivery, 2008, vol. 5, pp. 299-302.
Remy, J.S. et al.,'Targeted gene transfer into hepatoma cells with lipopolyamine-condensed DNA particles presenting galactose ligands: a stage towards artificial viruses', PNAS, 1995, val. 92, pp. 1744-1748.
Wolfrum C et al. "Mechanisms and optimization of in vivo delivery of lipophilic siRNAs" Nat. Biotechnol., 2007, vol. 25, No. 10, pp. 1149-1157.

*Primary Examiner* — J. E. Angell
(74) *Attorney, Agent, or Firm* — Kirk Ekena

(57) ABSTRACT

The present invention is directed compositions for targeted delivery of RNA interference (RNAi) polynucleotides to hepatocytes in vivo. Targeted RNAi polynucleotides are administered together with co-targeted delivery polymers. Delivery polymers provide membrane penetration function for movement of the RNAi polynucleotides from outside the cell to inside the cell. Reversible modification provides physiological responsiveness to the delivery polymers.

22 Claims, 7 Drawing Sheets

COMPOSITIONS FOR TARGETED DELIVERY OF SIRNA

CROSS-REFERENCE TO RELATED APPLICATIONS

This application is a divisional of U.S. application Ser. No. 13/032,029, filed 22 Feb. 2012, pending, which claims the benefit of U.S. Provisional Application No. 61307490, filed 24 Feb. 2010, which is hereby incorporated by reference in its entirety.

BACKGROUND OF THE INVENTION

The delivery of polynucleotide and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics preclude their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the nucleic acid dose required with these methods has been prohibitively large.

Numerous transfection reagents have been developed that achieve reasonably efficient delivery of polynucleotides to cells in vitro. However, in vivo delivery of polynucleotides using these same transfection reagents is complicated and rendered ineffective by in vivo toxicity, serum interactions, and poor targeting. Transfection reagents that work well in vitro, cationic polymers and lipids, typically form large electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for non-specific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction and poor bioavailability and targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less that 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit in vivo delivery by interfering with interactions necessary for targeting. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20040162260 demonstrated a means to reversibly regulate membrane disruptive activity of a membrane active polyamine. The membrane active polyamine provided a means of disrupting cell membranes. pH-dependent reversible regulation provided a means to limit activity to the endosomes of target cells, thus limiting toxicity. Their method relied on modification of amines on a polyamine with 2-propionic-3-methylmaleic anhydride.

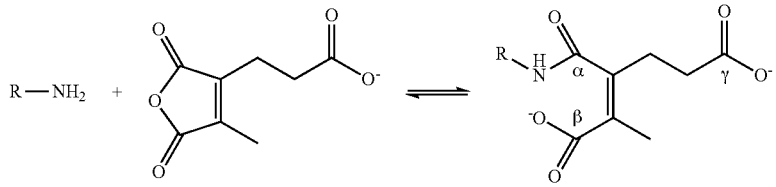

This modification converted the polycation to a polyanion via conversion of primary amines to pairs of carboxyl groups (β carboxyl and γ carboxyl) and reversibly inhibited membrane activity of the polyamine. Rozema et al. (Bioconjugate Chem. 2003, 14, 51-57) reported that the β carboxyl did not exhibit a full apparent negative charge and by itself was not able to inhibit membrane activity. The addition of the γ carboxyl group was reported to be necessary for effective membrane activity inhibition. To enable co-delivery of the nucleic acid with the delivery vehicle, the nucleic acid was covalently linked to the delivery polymer. They were able to show delivery of polynucleotides to cells in vitro using their biologically labile conjugate delivery system. However, because the vehicle was highly negatively charged, with both the nucleic acid and the modified polymer having high negative charge density, this system was not efficient for in vivo delivery. The negative charge likely inhibited cell-specific targeting and enhanced non-specific uptake by the reticuloendothelial system (RES). Also using the 2-propionic-3-methylmaleic anhydride-modified polymers, Rozema et al. demonstrated formation of small ternary electrostatic complexes of nucleic acids, polycations, and 2-propionic-3-methylmaleic anhydride-modified polymers.

Rozema et al., in U.S. Patent Publication 20080152661, improved on the method of U.S. Patent Publication 20040162260 by eliminating the high negative charge density of the modified membrane active polymer. By substituting neutral hydrophilic targeting (galactose) and steric stabilizing (PEG) groups for the γ carboxyl of 2-propionic-3-methylmaleic anhydride, Rozema et al. were able to retain overall water solubility and reversible inhibition of membrane activity while incorporating effective in vivo hepatocyte cell targeting. As before, the polynucleotide was covalently linked to the transfection polymer. Covalent attachment of the polynucleotide to the transfection polymer was maintained to ensure co-delivery of the polynucleotide with the transfection polymer to the target cell during in vivo administration by preventing dissociation of the polynucleotide from the transfection polymer. Co-delivery of the polynucleotide and transfection polymer was required because the transfection polymer provided for transport of the polynucleotide across a cell membrane, either from outside the cell or from inside an endocytic compartment, to the cell cytoplasm. U.S. Patent Publication 20080152661 demonstrated highly efficient delivery of polynucleotides, specifically RNAi oligonucleotides, to liver cells in vivo using this new improved physiologically responsive polyconjugate.

However, covalent attachment of the nucleic acid to the polyamine carries inherent limitations. Modification of the transfection polymers, to attach both the nucleic acid and the masking agents is complicated by charge interactions. Attachment of a negatively charged nucleic acid to a positively charged polymer is prone to aggregation thereby limiting the concentration of the mixture. Aggregation can be overcome by the presence of an excess of the polycation or polyanion. However, this solution limits the ratios in which the nucleic acid and the polymer may be formulated. Also, attachment of the negatively charged nucleic acid onto the unmodified cationic polymer causes condensation and aggregation of the complex and inhibits polymer modification. Modification of the polymer, forming a negative polymer, impairs attachment of the nucleic acid.

SUMMARY OF THE INVENTION

In a preferred embodiment, the invention features a composition for delivering an RNA interference polynucleotide to a liver cell in vivo comprising: an asialoglycoprotein receptor (ASGPr)-targeted reversibly masked membrane active polyamine (delivery polymer) and an RNA interference polynucleotide conjugated to a hydrophobic group containing at least 20 carbon atoms (RNA-conjugate). The delivery polymer and the siRNA-conjugate are synthesized separately and may be supplied in separate containers or a single container. The RNA interference polynucleotide is not conjugated to the polymer.

In a preferred embodiment, the invention features a composition for delivering an RNA interference polynucleotide to a liver cell in vivo comprising: an ASGPr-targeted reversibly masked membrane active polyamine (delivery polymer) and an RNA interference polynucleotide conjugated to a trivalent galactosamine (RNA conjugate). The delivery polymer and the siRNA-conjugate are synthesized separately and may be supplied in separate containers or a single container. The RNA interference polynucleotide is not conjugated to the polymer.

In a one embodiment, the membrane active polyamine comprises: an amphipathic polymer formed by random polymerization of amine-containing monomers and lower hydrophobic group-containing monomers. The amine-containing monomers contain pendant amine groups selected from the group consisting of: primary amine and secondary amine. The lower hydrophobic monomers contain pendent hydrophobic groups having 1-6 carbon atoms. The ratio of amine groups to hydrophobic groups is selected to form a water soluble polymer with membrane disruptive activity, preferably ≥1 amine monomer per hydrophobic monomer. In one embodiment the polymer will have 60-80% amine monomers. Hydrophobic groups may be selected from the group consisting of: alkyl group, alkenyl group, alkynyl group, aryl group, aralkyl group, aralkenyl group, and aralkynyl group, each of which may be linear, branched, or cyclic. Hydrophobic groups are preferably hydrocarbons, containing only carbon and hydrogen atoms. However, substitutions or heteroatoms which maintain hydrophobicity, and include, for example fluorine, may be permitted. Particularly suitable membrane active polyamines comprise poly(vinyl ether) random copolymers or poly(acrylate) random copolymers.

In a one embodiment, the membrane active polyamine comprises: an amphipathic polymer formed by random polymerization of amine-containing monomers, lower hydrophobic monomers, and higher hydrophobic monomers. The amine-containing monomers contain pendant amine groups selected from the group consisting of: primary amine and secondary amine. The lower hydrophobic monomers contain pendent hydrophobic groups having 1-6 carbon atoms. The higher hydrophobic monomers contain pendent hydrophobic groups having 12-36 or more carbon atoms. The ratio of amine groups to hydrophobic groups is selected to form a water soluble polymer with membrane disruptive activity, preferably ≥1 amine monomer per hydrophobic monomer. In one embodiment the polymer will have 60-80% amine monomers. Hydrophobic groups may be selected from the group consisting of: alkyl group, alkenyl group, alkynyl group, aryl group, aralkyl group, aralkenyl group, and aralkynyl group, each of which may be linear, branched, or cyclic, sterol, steroid, and steroid derivative. Hydrophobic groups are preferably hydrocarbons, containing only carbon and hydrogen atoms. However, substitutions or heteroatoms which maintain hydrophobicity, and include, for example fluorine, may be permitted. Particularly suitable membrane active polyamines comprise poly(vinyl ether) random terpolymers or poly(acrylate) random terpolymers.

In a preferred embodiment, a reversibly masked membrane active polyamine comprises a membrane active polyamine of the invention reversibly modified by reaction of amines on the polymer with masking agents. An amine is reversibly modified if cleavage of the modifying group restores the amine. Reversible modification of the membrane active polyamine reversibly inhibits membrane activity of the membrane active polyamine. Preferably, a masking agent also provides targeting function and/or serum interaction avoidance function. Modification of polymer amine with the masking agent also preferably neutralizes the charge of the amine. A preferred masking agent comprises a galactosamine or galactosamine derivative or a polyethylene glycol having a disubstituted maleic anhydride amine-reactive group. Reaction of the anhydride with an amine reversibly modifies the amine to form a maleamate or maleamic acid. In the masked state, the reversibly masked membrane active polyamine does not exhibit membrane disruptive activity. Reversible modification of more than 50%, more than 55%, more than 60%, more than 65%, more than 70%, more than 75%, or more than 80%, of the amines on the polyamine with masking agents may be required to inhibit membrane activity and provide cell targeting function, i.e. form a reversibly masked membrane active polymer. Membrane activity inhibition and/or in vivo targeting of the described membrane active polyamines requires modification of >50% of the polymer amines.

A preferred masking agent comprises a neutral hydrophilic substituted alkylmaleic anhydride:

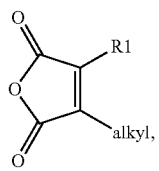

wherein R1 comprises a targeting moiety or a steric stabilizer. An example of a substituted alkylmaleic anhydride consists of a 2-propionic-3-alkylmaleic anhydride derivative. A neutral hydrophilic 2-propionic-3-alkylmaleic anhydride derivative is formed by attachment of a neutral hydrophilic group to a 2-propionic-3-alkylmaleic anhydride through the 2-propionic-3-alkylmaleic anhydride γ-carboxyl group. In one embodiment, the alkyl group consists of a methyl group.

A preferred masking agent provides targeting function through affinity for cell surface receptors, i.e. the masking agent contains a ligand for a cell surface receptor. Preferred masking agents contain saccharides having affinity for the ASGPr, including but not limited to: galactose, N-Acetylgalactosamine and galactose derivatives. Galactose derivatives having affinity for the ASGPr are well known in the art. An essential feature of the reversibly modified membrane active polyamine is that at least some, and as many as all, of the masking agents attached to a polymer provide cell targeting function. Another preferred masking agent provides improved bio-distribution through inhibition of non-specific interactions between the reversibly modified polymer and serum components or non-target cells and by reducing aggregation of the polymer. Preferred masking agents having steric stabilizer function include, but not limited to, polyethylene glycols. In one embodiment, a combination of targeting and steric stabilizer masking agents are used.

The RNAi polynucleotide conjugate and delivery polymer are administered to a mammal in pharmaceutically acceptable carriers or diluents. In one embodiment, the delivery polymer and the RNAi polynucleotide conjugate may be combined in a solution prior to administration to the mammal. In another embodiment, the delivery polymer and the RNAi polynucleotide conjugate may be co-administered to the mammal in separate solutions. In yet another embodiment, the delivery polymer and the RNAi polynucleotide conjugate may be administered to the mammal sequentially. For sequential administration, the delivery polymer may be administered prior to administration of the RNAi polynucleotide conjugate. Alternatively, for sequential administration, the RNAi polynucleotide conjugate may be administered prior to administration of the delivery polymer.

Further objects, features, and advantages of the invention will be apparent from the following detailed description when taken in conjunction with the accompanying drawings.

DETAILED DESCRIPTION OF THE INVENTION

Figure 1:
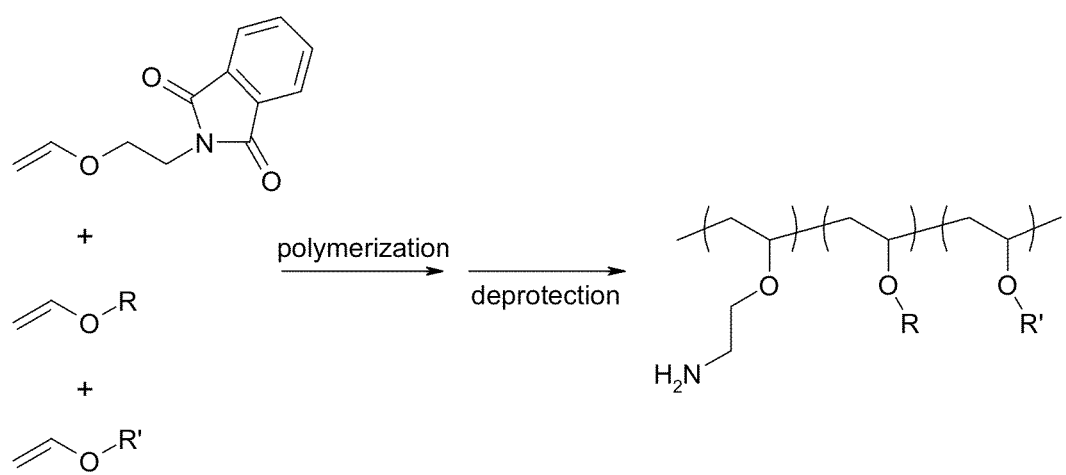
FIG. 1. Reaction scheme for polymerization of amphipathic poly(vinyl ether) random terpolymers.

Described herein is an improved method for delivering RNA interference (RNAi) polynucleotides, to liver cells in a mammal in vivo. The method also provides for improved methods of production of RNAi polynucleotide delivery vehicles. Previously, in vivo delivery of polynucleotides required physical association of the polynucleotide with the delivery vehicle. The polynucleotide was either electrostatically associated with a delivery vehicle, as in polycation/nucleic acid complexes, encapsulated by the delivery vehicle, as in liposomes and stable nucleic acid-lipid particles (SNALPs), or covalently linked to a delivery vehicle, as in Dynamic PolyConjugates (Rozema et al. 2007). Surprisingly, we have found that by using appropriate RNAi polynucleotide conjugate molecules and appropriately targeted delivery polymers, the RNAi polynucleotide can be separated from the delivery polymer and still achieve efficient hepatocyte delivery of the polynucleotide.

The ability to separate the polynucleotide from the delivery polymer provides advantages in formulation, synthesis, and manufacturing.

a) By removing the requirement that the polynucleotide and polymer are associated, either by covalent linkage or by charge-charge interaction, the concentration of the polymers and polynucleotides and the ratio between them is limited only by the solubility of the components rather than the solubility of the associated complex or ability to manufacture the complex. Increased solubility permits increased polynucleotide or delivery polymer concentration and therefore increased dosage.

b) The polynucleotide and delivery polymer may be mixed at anytime prior to administration, or even administered separately. Thus, separation allows the components to be stored separately, either in solution or dry.

c) Smaller, more stable formulation is possible compared to the larger, inherently unstable non-covalent delivery systems.

d) Manufacture of the masked delivery polymer is easier in the absence of a covalently attached negatively charged polynucleotide or the need to covalently attach a negatively charged polynucleotide.

e) Manufacture is simplified and requires fewer steps in absence of physical association of the polynucleotide with the delivery polymer.

f) Improvements in targeting of the siRNA and polymer are observed.

The invention includes conjugate delivery systems of the general structure:

wherein N is a RNAi polynucleotide, T is a polynucleotide targeting moiety (either a hydrophobic group having 20 or more carbon atoms or a galactose cluster), P is a membrane active polyamine, and masking agent $M^1$ contains a targeting moiety, a galactose or galactose derivative having affinity for the asialoglycoprotein receptor, covalently linked to P via a physiologically reversible linkage L, such as a maleamate linkage. Cleavage of L restores an unmodified amine on polyamine P. Masking agent $M^2$ is optional. If present, $M^2$ is a hydrophilic steric stabilizer covalently linked to P via a physiologically reversible linkage L, such as a maleamate linkage. x and y are each integers. In its unmodified state, P is a membrane active polyamine. Delivery polymer $(M^1-L)_x-P-(L-M)_y$ is not membrane active. Reversible modification of P amines, by attachment of $M^1$ and optionally $M^2$, reversibly inhibits or inactivates membrane activity of P and reduces the net positive charge of P. Sufficient masking agents are attached to P to inhibit membrane activity of the polymer. x+y has a value greater than 50%, more preferably greater than 60%, and more preferably greater than 70% of the amines on polyamine P, as determined by the quantity of amines on P in the absence of any masking agents. Upon cleavage of reversible linkages L, unmodified amines are restored thereby reverting P to its unmodified, membrane active state. The reversible bond of reversible linkage L is chosen such that cleavage occurs in a desired physiological condition, such as that present in a desired tissue, organ, or sub-cellular location. A preferred reversible linkage is a pH labile linkage. $(M^1-L)_x-P-(L-M^2)_y$, an ASGPr-targeted reversibly masked membrane active polymer (masked polymer), and T-N, a polynucleotide-conjugate, are synthesized or manufactured separately. Neither T nor N are covalently linked directly or indirectly to P, L, $M^1$ or $M^2$. Electrostatic or hydrophobic association of the polynucleotide or the polynucleotide-conjugate with the masked or unmasked polymer is not required for in vivo liver delivery of the polynucleotide. The masked polymer and the polynucleotide conjugate can be supplied in the same container or in separate containers. They may be combined prior to administration, co-administered, or administered sequentially.

Polymer

The polymers of the invention are amphipathic membrane active polyamines. A polymer is a molecule built up by repetitive bonding together of smaller units called monomers. A polymer can be a homopolymer in which a single monomer is used or a polymer can be copolymer or heteropolymer in which two or more different monomers are used. The main chain of a polymer is composed of the atoms whose bonds are required for propagation of polymer length. A side chain of a polymer is composed of the atoms whose bonds are not required for propagation of polymer length.

More specifically, the polymers of the invention are amphipathic membrane active random copolymers. The monomers in random copolymers do not have a defined or arrangement along the main chain, and are written, for example, as: -A-$B_y$— or -$A_x$-$B_y$—$C_z$—. The general compositions of such polymers are reflective of the ratio of input monomers. However, the exact ratio of one monomer to another may differ between chains. The distribution of monomers may also differ along the length of a single polymer. Also, the chemical properties of a monomer may affect its rate of incorporation into a random copolymer and its distribution within the polymer. While the ratio of monomers in a random polymer is dependent on the input ratio of monomer, the input ratio may not match exactly the ratio of incorporated monomers.

Amphipathic

Amphipathic, or amphiphilic, polymers are well known and recognized in the art and have both hydrophilic (polar, water-soluble) and hydrophobic (non-polar, lipophilic, water-insoluble) groups or parts.

Hydrophilic groups indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

Hydrophobic groups indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

As used herein, a surface active polymer lowers the surface tension of water and/or the interfacial tension with other phases, and, accordingly, is positively adsorbed at the liquid/vapor interface. The property of surface activity is usually due to the fact that the molecules of the substance are amphipathic or amphiphilic.

Membrane Active

As used herein, membrane active polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic

Endosomolytic polymers are polymers that, in response to a change in pH, are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties over a physiologically relevant pH range (usually pH 5.5-8). This shift can be a change in the polymer's solubility or ability to interact with other compounds or membranes as a result in a shift in charge, hydrophobicity, or hydrophilicity. Exemplary endosomolytic polymers have pH-labile groups or bonds. A reversibly masked membrane active polymer, wherein the masking agents are attached to the polymer via pH labile bonds, can therefore be considered to be an endosomolytic polymer.

Amphipathic Membrane Active Random Copolymers

Amphipathic membrane active polyamines of the invention comprise: amphipathic membrane active polyamines (random heteropolymers).

For copolymers of the invention, the two or more monomeric species consist minimally of: a monomer containing a pendant primary or secondary amine group and a monomer containing a pendant hydrophobic pendent group. In a more preferred embodiment, the two monomer species consist minimally of: a monomer containing a pendant primary or secondary amine group and a monomer containing a pendant lower hydrophobic pendent group. As used herein, a pendant group is a group composed of the atoms linked to a polymer but whose bonds are not required for propagation of polymer length, i.e., neither the atoms nor bonds of a pendant group are part of the main chain or backbone of a polymer to which the group is attached.

Amphipathic membrane active polyamine copolymers of the invention are the product of copolymerization of two or more monomer species. In one embodiment, amphipathic membrane active heteropolymers of the invention have the general structure:

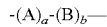
—$(A)_a$-$(B)_b$— wherein, A contains a pendent primary or secondary amine functional group and B contains a lower hydrophobic pendant group (containing 2 to about 6 carbon atoms). a and b are integers >0. To aid in synthesis, protected amine containing monomers, such as phthalimido-protected or BOC-protected amine monomers may be used during polymerization. The amine protecting groups are removed after polymerization to yield amines. The incorporation of monomers, up to 10%, containing pendant medium or higher hydrophobic groups (7 or more carbon atoms) is permissible. The incorporation of additional monomeric species in minor amounts (<5%) is also permissible. For example, polymers may also have additional reactive group-containing monomers. Reactive group-containing monomers may be used to attach components to the polymer following synthesis of the polymer. A monomer can have a reactive group that does not participate in the polymerization reaction. A monomer can also have a reactive group that is protected. The protection group prevents reaction of the reactive group during polymerization. After polymerization, the protection group is removed.

In another embodiment a terpolymer, a polymer having at least three different monomeric species, is used as the delivery polymer. For terpolymers of the invention, the three monomeric species consist minimally of: a monomer containing a pendant primary or secondary amine group, a monomer containing a first pendant hydrophobic group, and a monomer containing a second pendant hydrophobic group wherein the first and second hydrophobic pendent groups are different. In a more preferred embodiment, the three or more monomers species consist minimally of: a monomer containing a primary or secondary amine group, a monomer containing a pendant lower hydrophobic group, and a monomer containing a pendant medium or higher hydrophobic group.

In one embodiment, amphipathic membrane active terpolymers of the invention have the general structure:

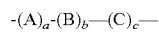
—$(A)_a$-$(B)_b$—$(C)_c$— wherein, A contains a pendent primary or secondary amine functional group, B contains a pendant lower hydrophobic group (containing 2 to about 6 carbon atoms), and C contains a pendant higher hydrophobic group (containing 12 or more carbon atoms). a, b, and c are integers >0. To aid in synthesis, protected amine-containing monomers, such as phthalimido-protected or BOC-protected amine monomers may be used during polymerization. The amine protecting groups are removed after polymerization to yield amines. The incorporation of additional monomeric species in minor amounts (<5%) is possible. For example, polymers may also have additional hydrophobic monomers or reactive group-containing monomers. Reactive group-containing monomers may be used to attach components to the polymer following synthesis of the polymer. A monomer can have a reactive group that does not participate in the polymerization reaction. A monomer can also have a reactive group that is protected. The protection group prevents reaction of the reactive group during polymerization. After polymerization, the protection group is removed.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives. As used herein, lower hydrophobic monomers or groups comprise hydrophobic groups having two (2) to six (6) carbon atoms. As used herein, medium hydrophobic monomers or groups comprise hydrophobic groups having seven (7) to eleven (11) carbon atoms. As used herein, higher hydrophobic monomers or groups comprise hydrophobic groups having twelve (12) to thirty-sic (36) or more carbon atoms.

The biophysical properties of the amphipathic polymers are determined by the classes of monomer species polymerized, the ratio at which they are incorporated into the polymer, and the size of the polymer. Different polymers can be made by altering the feed ratio of monomers in the polymerization reaction or altering the groups used to modify a polymer backbone. While the incorporated ratio of monomers in a polymer can be the same as the feed ratio of monomers, the ratios can be different. Whether the monomers are incorporated at the feed ratio or at a different ratio, it is possible to alter the feed ratio of monomers to achieve a desired monomer incorporation ratio.

The ratio of amine groups to hydrophobic groups is selected to form a water soluble polymer with membrane disruptive activity. Preferred membrane active polymers of the invention are water soluble at ≥1 mg/ml, ≥5 mg/ml, ≥10 mg/ml, ≥15 mg/ml, ≥20 mg/ml, ≥25 mg/ml, and ≥30 mg/ml. Preferred membrane active polymers of the invention are surface active. Membrane active polymers of the invention are preferably in the size range of about 3 kDa to about 300 kDa. Because the polymers are amphipathic, they self-associate in aqueous solution, with a critical association concentration ≤1 mg/ml.

In one embodiment, the monomer incorporation ratio for the membrane active polyamine copolymers is about 4-8 amine monomers:3-5 lower hydrophobic monomers. In another embodiment, the monomer incorporation ratio for the membrane active polyamines is about 5.4-7.5 amine monomers:3-3.5 lower hydrophobic monomers. In another embodiment, the monomer incorporation ratio for the membrane active polyamines is about 2 amine monomers to about 1 lower hydrophobic monomers. In one embodiment the hydrophobic groups of the hydrophobic monomers consist of alkyl groups.

In one embodiment, the monomer incorporation ratio for the membrane active polyamine terpolymers is about 4-8 amine monomers:3-5 lower hydrophobic monomers:1 higher hydrophobic monomer. In another embodiment, the monomer incorporation ratio for the membrane active polyamines is about 5.4-7.5 amine monomers:3-3.5 lower hydrophobic monomers:1 higher hydrophobic monomers. In another embodiment, the monomer incorporation ratio for the membrane active polyamines is about 6 amine monomers to about 3 lower hydrophobic monomers to about 1 higher hydrophobic monomer. In one embodiment the hydrophobic groups of the hydrophobic monomers consist of alkyl groups.

In one embodiment, the amine/lower hydrophobic group copolymers are synthesized using monomers at a feed ratio of about 4-8 amine monomer:about 3-5 lower alkyl monomer. In another embodiment, the amine/lower hydrophobic group copolymers can be synthesized using monomers at a feed ratio of about 15 amine monomer:4 lower hydrophobic group monomer.

In one embodiment, the amine/lower hydrophobic group/higher hydrophobic group terpolymers are synthesized using monomers at a feed ratio of about 4-8 amine monomer:about 3-5 lower alkyl monomer:1 higher alkyl monomer. In another embodiment, the amine/lower hydrophobic group/higher hydrophobic group terpolymers can be synthesized using monomers at a feed ratio of about 15 amine monomer:4 lower hydrophobic group monomer:1 higher hydrophobic group monomer.

In one embodiment, particularly suitable membrane active polyamines comprise copolymers having amine containing monomers, butyl-containing monomers and higher hydrophobic group-containing monomers wherein the higher hydrophobic group contains 12-18 carbon atoms. Particularly suitable membrane active polyamines comprise poly(vinyl ether) random terpolymers or poly(acrylate) random terpolymers.

In another embodiment, particularly suitable membrane active polyamines comprise copolymers having amine containing monomers, lower hydrophobic group-containing monomers. Particularly suitable membrane active polyamines comprise poly(vinyl ether) random copolymers or poly(acrylate) random copolymers.

Particularly suitable membrane active polyamines comprise copolymers having amine containing monomers and butyl-containing monomers. Particularly suitable membrane active polyamines comprise poly(vinyl ether) random copolymers or poly(acrylate) random copolymers.

Biodegradable Polymers

A polymer may have one or more cleavable bonds. If the cleavable bonds are naturally cleaved under physiological conditions or cellular physiological conditions, the polymer is biodegradable. The biodegradable bond may either be in the main-chain or in a side chain. If the cleavable bond occurs in the main chain, cleavage of the bond results in a decrease in polymer length and the formation of two molecules. If the cleavable bond occurs in the side chain, then cleavage of the bond results in loss of side chain atoms from the polymer. For membrane active polymers, biodegradation of the polymer will result in decreased membrane activity of the polymer. As used herein, the term biodegradable means that the polymer will degrade over time by the action of enzymes, by hydrolytic action and/or by other similar mechanisms in the body. Biodegradable bonds are those bonds which are cleaved by biological processes and include, but are not limited to: esters, phosphodiesters, certain peptide bonds and combinations thereof. Esters undergo hydrolysis and are also catalytically cleaved by esterases. Phosphodiesters are cleaved by nucleases. Peptide bonds are cleaved by peptidases. In particular, the polymer backbone is degraded or cleaved, or side chains (pendent groups) are degraded or cleaved, from the polymer. Biodegradable bonds in the biodegradable polymers may be cleaved, under physiological conditions with a half life of less than 45 min, more than 45 minutes, more than 2 hours, more than 8 hours, more than 24 hours, or more than 48 hours. While biodegradable polymers are useful for in vivo delivery, the polymer must be sufficiently stable to form a sufficiently sized polymer in aqueous solution. Also, the rate of cleavage of a biodegradable bond must be slower than the labile bond used to attach a masking agent to the polymer. In a preferred embodiment, degradation of a biodegradable polymer occurs at a slower rate than cleavage of the masking agents.

Masking

The delivery polymers of the invention comprise reversibly modified amphipathic membrane active polyamines wherein reversible modification inhibits membrane activity, neutralizes the polyamine to reduce positive charge and form a near neutral charge polymer, provides cell-type specific targeting, and inhibits non-specific interactions of the polymer. The polyamine is reversibly modified through reversible modification of amines on the polyamine.

The membrane active polyamines of the invention are capable of disrupting plasma membranes or lysosomal/endocytic membranes. This membrane activity is an essential feature for cellular delivery of the polynucleotide. Membrane activity, however, leads to toxicity when the polymer is administered in vivo. Polyamines also interact readily with many anionic components in vivo, leading to undesired biodistribution. Therefore, reversible masking of membrane activity of the polyamine is necessary for in vivo use. This masking is accomplished through reversible attachment of masking agents to the membrane active polyamine to form a reversibly masked membrane active polymer, i.e. a delivery polymer. In addition to inhibiting membrane activity, the masking agents shield the polymer from non-specific interactions, reduce serum interactions, increase circulation time, and provide cell-specific interactions, i.e. targeting.

It is an essential feature of the masking agents that, in aggregate, they inhibit membrane activity of the polymer, shield the polymer from non-specific interactions (reduce serum interactions, increase circulation time), and provide in vivo hepatocyte targeting. The membrane active polyamine is membrane active in the unmodified (unmasked) state and not membrane active (inactivated) in the modified (masked) state. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. Masking requires modification of ≥50%, ≥60%, ≥70%, or ≥80% of the amine groups on the polymer, as determined by the quantity of amines on the polymer in the absence of any masking agents. It is also a preferred characteristic of masking agents that their attachment to the polymer reduces positive charge of the polymer, thus forming a more neutral delivery polymer. It is desirable that the masked polymer retain aqueous solubility.

As used herein, a membrane active polyamine is masked if the modified polymer does not exhibit membrane activity and exhibits cell-specific (i.e. hepatocyte) targeting in vivo. A membrane active polyamine is reversibly masked if cleavage of bonds linking the masking agents to the polymer results in restoration of amines on the polymer thereby restoring membrane activity.

It is another essential feature that the masking agents are covalently bound to the membrane active polyamine through physiologically reversible bonds. By using physiologically reversible linkages or bonds, the masking agents can be cleaved from the polymer in vivo, thereby unmasking the polymer and restoring activity of the unmasked polymer. By choosing an appropriate reversible linkage, it is possible to form a conjugate that restores activity of the membrane active polymer after it has been delivered or targeted to a desired cell type or cellular location. Reversibility of the linkages provides for selective activation of the membrane active polymer. Reversible covalent linkages contain reversible or labile bonds which may be selected from the group comprising: physiologically labile bonds, cellular physiologically labile bonds, pH labile bonds, very pH labile bonds, and extremely pH labile bonds.

As used herein, a masking agent comprises a compound having an ASGPr targeting moiety or a steric stabilizer and an amine-reactive group wherein reaction of the amine-reactive group with an amine on a polymer results in linkage of the ASGPr targeting moiety or steric stabilizer to the polymer via a physiologically labile covalent bond. An ASGPr targeting moiety is a group, typically a saccharide, having affinity for the asialoglycoprotein receptor. A preferred steric stabilizer is a polyethylene glycol (PEG). Preferred masking agents of the invention are able to modify the polymer (form a reversible bond with the polymer) in aqueous solution. A preferred amine-reactive group comprises a disubstituted maleic anhydride. A preferred masking agent is represented by the structure:

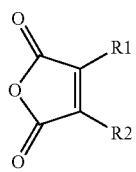

wherein in which $R^1$ is an alkyl group such as a methyl (—$CH_3$) group, ethyl (—$CH_2CH_3$) group, or propyl (—$CH_2CH_2CH_3$) group (to form a substituted alkylmaleic anhydride), and $R^2$ comprises an asialoglycoprotein receptor (ASGPr) targeting moiety or a steric stabilizer.

The membrane active polyamine can be conjugated to masking agents in the presence of an excess of masking agents. The excess masking agent may be removed from the conjugated delivery polymer prior to administration of the delivery polymer.

Steric Stabilizer

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. As used herein, steric stabilizers prevent or inhibit intramolecular or intermolecular interactions of a polymer to which it is attached relative to the polymer containing no steric stabilizer in aqueous solution.

ASGPr Targeting Moiety

Targeting moieties or groups enhance the pharmacokinetic or biodistribution properties of a conjugate to which they are attached to improve cell-specific distribution and cell-specific uptake of the conjugate. Galactose and galactose derivates have been used to target molecules to hepatocytes in vivo through their binding to the asialoglycoprotein receptor (ASGPr) expressed on the surface of hepatocytes. As used herein, a ASGPr targeting moiety comprises a galactose and galactose derivative having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes.

ASGPr targeting moieties may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoyl-galactosamine (Iobst, S. T. and Drickamer, K. *J.B.C.* 1996, 271, 6686). ASGPr targeting moieties can be monomeric (e.g., having a single galactosamine) or multimeric (e.g., having multiple galactosamines).

In some embodiments, the galactose targeting moiety is linked to the amine-reactive group through a PEG linker as illustrated by the structure:

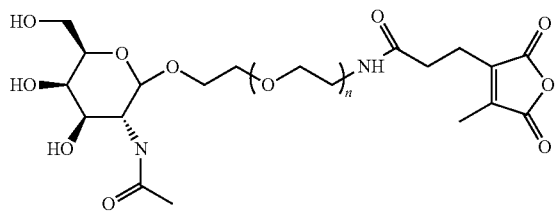

wherein n is an integer between 1 and 19.

In one embodiment, the membrane active polyamine is reversibly masked by attachment of ASGPr targeting moiety masking agents to ≥50%, ≥60%, ≥70%, or ≥80% of amines on the polyamine. In another embodiment, the membrane active polyamine is reversibly masked by attachment of ASGPr targeting moiety masking agents and PEG masking agents to ≥50%, ≥60%, ≥70%, or ≥80% of amines on the polyamine. In another embodiment, the ASGPr targeting moiety masking agents comprise an ASGPr targeting moiety linked to an amine-reactive group via a PEG linker. For membrane active polyamine masking with both ASGPr targeting moiety masking agents and PEG masking agents, a ratio of PEG to ASGPr targeting moiety is about 0-4:1, more preferably about 0.5-2:1. In another embodiment, there are about 1.3-2 PEG masking agents to about 1 galactose derivative masking agent.

Surface Charge

Zeta potential is a physical property which is exhibited by a particle in suspension and is closely related to surface charge. In aqueous media, the pH of the sample is one of the most important factors that affects zeta potential. When charge is based upon protonation/deprotonation of bases/acids, the charge is dependent on pH. Therefore, a zeta potential value must include the solution conditions, especially pH, to be meaningful. For typical particles, the magnitude of the zeta potential gives an indication of the potential stability of the colloidal system. If all the particles in suspension have a large negative or positive zeta potential, they will tend to repel each other and there will be no tendency for the particles to come together. However, if the particles have low zeta potential values, there will be no force to prevent the particles coming together and flocculating. The general dividing line between stable and unstable suspensions for typical particles is generally taken at either +30 or −30 mV. Particles with zeta potentials more positive than +30 mV or more negative than −30 mV are normally considered stable. Delivery polymers of the described invention exhibit a zeta potential of 20 mV to −20 mV at physiological salt and pH 8, but are colloidally stable in aqueous solution and do not flocculate.

Positive charge, or zeta potential, of a membrane active polyamine is reduced by modification with the masking agents. Polymer charge, especially positive charge, can result in unwanted interactions with serum components or non-target cells. Positive surface charge also plays a role in membrane activity by enhancing interaction of the polymer with negatively charged cell membranes. Therefore, delivery polymers with near neutral net charge or zeta potential are preferred for in vivo delivery of polynucleotides. Delivery polymers of the invention, membrane active polyamines masked by reversible attachment of ASGPr targeting moiety masking agents and steric stabilizer masking agents, have an apparent surface charge near neutral and are serum stable. More specifically, the delivery polymers of the invention have a zeta potential, measured at pH 8, between +30 and −30 mV, between +20 and −20 mV, between +10 and −10 mV, or between +5 and −5 mV. At pH 7, the net charge of the conjugate is expected to be more positive than at pH 8. Net charge, or surface charge, is a significant factor for in vivo applications.

Labile Linkage

A linkage or linker is a connection between two atoms that links one chemical group or segment of interest to another chemical group or segment of interest via one or more covalent bonds. For example, a linkage can connect a masking agent to a polymer. Formation of a linkage may connect two separate molecules into a single molecule or it may connect two atoms in the same molecule. The linkage may be charge neutral or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A reversible or labile bond is a covalent bond other than a covalent bond to a hydrogen atom that is capable of being selectively broken or cleaved under conditions that will not break or cleave other covalent bonds in the same molecule. More specifically, a reversible or labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, reversible or labile bonds encompass bonds that can be selectively cleaved more rapidly than other bonds in a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent. Physiologically labile bonds that are cleaved under appropriate conditions with a half life of less than 45 min. are considered very labile. Physiologically labile bonds that are cleaved under appropriate conditions with a half life of less than 15 min are considered extremely labile.

Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

As used herein, a pH-labile bond is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile.

Reaction of an anhydride with an amine forms an amide and an acid. For many anhydrides, the reverse reaction (formation of an anhydride and amine) is very slow and energetically unfavorable. However, if the anhydride is a cyclic anhydride, reaction with an amine yields an amide acid, a molecule in which the amide and the acid are in the same molecule. The presence of both reactive groups (the amide and the carboxylic acid) in the same molecule accelerates the reverse reaction. In particular, the product of primary amines with maleic anhydride and maleic anhydride derivatives, maleamic acids, revert back to amine and anhydride $1 \times 10^9$ to $1 \times 10^{13}$ times faster than its noncyclic analogues (Kirby 1980).

Reaction of an amine with an anhydride to form an amide and an acid.

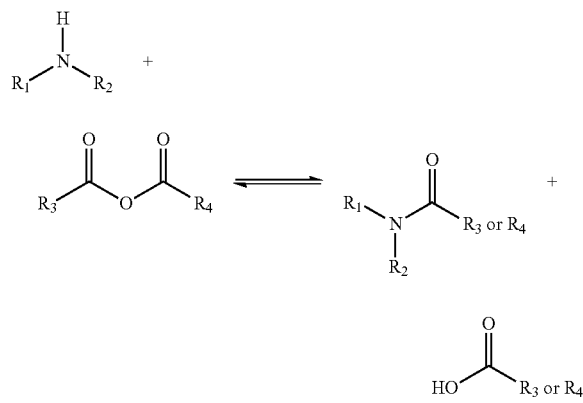

Reaction of an amine with a cyclic anhydride to form an amide acid.

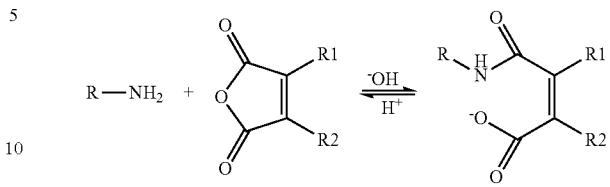

Cleavage of the amide acid to form an amine and an anhydride is pH-dependent and is greatly accelerated at acidic pH. This pH-dependent reactivity can be exploited to form reversible pH-labile bonds and linkers. Cis-aconitic acid has been used as such a pH-sensitive linker molecule. The γ-carboxylate is first coupled to a molecule. In a second step, either the α or β carboxylate is coupled to a second molecule to form a pH-sensitive coupling of the two molecules. The half life for cleavage of this linker at pH 5 is between 8 and 24 h.

Structures of cis-aconitic anhydride and maleic anhydride.

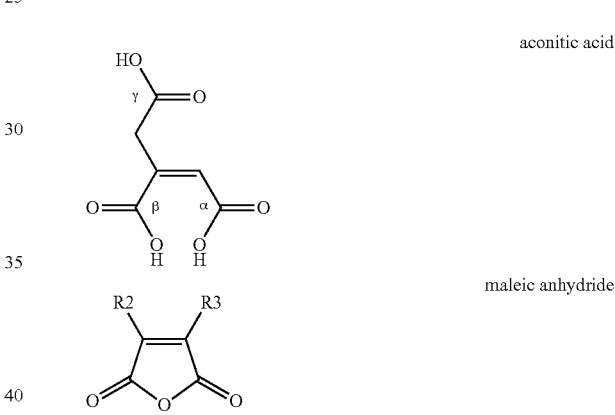

The pH at which cleavage occurs is controlled by the addition of chemical constituents to the labile moiety. The rate of conversion of maleamic acids to amines and maleic anhydrides is strongly dependent on substitution (R2 and R3) of the maleic anhydride system. When R2 is methyl, the rate of conversion is 50-fold higher than when R2 and R3 are hydrogen. When there are alkyl substitutions at both R2 and R3 (e.g., 2,3-dimethylmaleicanhydride) the rate increase is dramatic: 10.000-fold faster than non-substituted maleic anhydride. The maleamate bond formed from the modification of an amine with 2,3-dimethylmaleic anhydride is cleaved to restore the anhydride and amine with a half-life between 4 and 10 min at pH 5. It is anticipated that if R2 and R3 are groups larger than hydrogen, the rate of amide-acid conversion to amine and anhydride will be faster than if R2 and/or R3 are hydrogen.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Disubstituted cyclic anhydrides are particularly useful for attachment of masking agents to membrane active polyamines of the invention. They provide physiologically pH-labile linkages, readily modify amines, and restore those amines upon cleavage in the reduced pH found in cellular endosomes and lysosome. Second, the α or β carboxylic acid group created upon reaction with an amine, appears to contribute only about 1/20$^{th}$ of the expected negative charge to the polymer (Rozema et al. Bioconjugate Chemistry 2003). Thus, modification of the polyamine with the disubstituted maleic anhydrides effectively neutralizes the positive charge of the polyamine rather than creates a polymer with high negative charge. Near neutral polymers are preferred for in vivo delivery.

Step Polymerization

In step polymerization, the polymerization occurs in a stepwise fashion. Polymer growth occurs by reaction between monomers, oligomers, and polymers. No initiator is needed since the same reaction occurs throughout, and there is no termination step so that the end groups are still reactive. The polymerization rate decreases as the functional groups are consumed.

A polymer can be created using step polymerization by using monomers that have two reactive groups (A and B) in the same monomer (heterobifunctional), wherein A comprises a reactive group and B comprises an A-reactive group (a reactive group which forms a covalent bond with A). Polymerization of A-B yields -[A-B]$_n$—. Reactive groups A and B can be joined by a covalent bond or a plurality of covalent bonds, thereby forming the polymer monomer. A polymer can also be created using step polymerization by using homo-bifunctional monomers such that A-A+B—B yields -[A-A-B—B]$_n$—. Generally, these reactions can involve acylation or alkylation. The two reactive groups of a monomer can be joined by a single covalent bond or a plurality of covalent bonds.

If reactive group A is an amine then B is an amine-reactive group, which can be selected from the group comprising: isothiocyanate, isocyanate, acyl azide, N-hydroxy-succinimide, sulfonyl chloride, aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, acid halide, p-nitrophenyl ester, o-nitrophenyl ester, pentachlorophenyl ester, pentafluorophenyl ester, carbonyl imidazole, carbonyl pyridinium, and carbonyl dimethylaminopyridinium. In other terms, when reactive group A is an amine then B can be an acylating or alkylating agent or amination agent.

If reactive group A is a sulfhydryl(thiol) then B is a thiol-reactive group, which can be selected from the group comprising: iodoacetyl derivative, maleimide, aziridine derivative, acryloyl derivative, fluorobenzene derivative, and disulfide derivative (such as a pyridyl disulfide or 5-thio-2-nitrobenzoic acid (TNB) derivative).

If reactive group A is carboxylate then reactive group B is a carboxylate-reactive group, which can be selected from the group comprising: diazoacetate and an amine in which a carbodiimide is used. Other additives may be utilized such as carbonyldiimidazole, dimethylamino pyridine (DMAP), N-hydroxysuccinimide or alcohol using carbodiimide, and DMAP.

If reactive group A is a hydroxyl then reactive group B is a hydroxyl-reactive group, which can be selected from the group comprising: epoxide, oxirane, activated carbamate, activated ester, and alkyl halide.

If reactive group A is an aldehyde or ketone then reactive group B is an aldehyde- or ketone-reactive group, which can be selected from the group comprising: hydrazine, hydrazide derivative, amine (to form a Schiff Base that may or may not be reduced by reducing agents such as NaCNBH$_3$), and hydroxyl compound.

A polymer can be created using step polymerization by using bifunctional monomers and another agent such that A-A plus another agent yields -[A-A]$_n$-.

If reactive group A is a sulfhydryl(thiol) group then it can be converted to disulfide bonds by oxidizing agents such as iodine (I$_2$), sodium periodate (NalO$_4$), or oxygen (O$_2$). If reactive group A can is an amine, it can be converted to a thiol by reaction with 2-Iminothiolate (Traut's reagent) which then undergoes oxidation and disulfide formation. Disulfide derivatives (such as a pyridyl disulfide or TNB derivatives) can also be used to catalyze disulfide bond formation.

Reactive groups A or B in any of the above examples can also be a photoreactive group such as aryl azide (including halogenated aryl azide), diazo, benzophenone, alkyne, or diazirine derivative.

Reactions of the amine, hydroxyl, sulfhydryl, or carboxylate groups yield chemical bonds that are described as amides, amidines, disulfides, ethers, esters, enamines, imines, ureas, isothioureas, isoureas, sulfonamides, carbamates, alkylamine bonds (secondary amines), and carbon-nitrogen single bonds in which the carbon is boned to a hydroxyl group, thioether, diol, hydrazone, diazo, or sulfone.

Chain Polymerization

In chain-reaction polymerization, growth of the polymer occurs by successive addition of monomer units to a limited number of growing chains. The initiation and propagation mechanisms are different, and there is typically a chain-terminating step. Chain polymerization reactions can be radical, anionic, or cationic. Monomers for chain polymerization may be selected from the groups comprising: vinyl, vinyl ether, acrylate, methacrylate, acrylamide, and methacrylamide groups. Chain polymerization can also be accomplished by cycle or ring opening polymerization. Several different types of free radical initiators can be used including, but not limited to, peroxides, hydroxy peroxides, and azo compounds such as 2,2'-Azobis(-amidinopropane)dihydrochloride (AAP).

A naturally occurring polymer is a polymer that can be found in nature. Examples include polynucleotides, proteins, collagen, and polysaccharides (starches, cellulose, glycosaminoglycans, chitin, agar, agarose). A natural polymer can be isolated from a biological source or it can be synthetic. A synthetic polymer is formulated or manufactured by a chemical process "by man" and is not created by a naturally occurring biological process. A non-natural polymer is a synthetic polymer that is not made from naturally occurring (animal or plant) materials or monomers (such as amino acids, nucleotides, and saccharides). A polymer may be fully or partially natural, synthetic, or non-natural.

RNAi Polynucleotide Conjugate

We have found that conjugation of an RNAi polynucleotide to a polynucleotide targeting moiety, either a hydrophobic group or to a galactose cluster, and co-administration of the RNAi polynucleotide conjugate with the delivery polymer described above provides for efficient, functional delivery of the RNAi polynucleotide to liver cells, particularly hepatocytes, in vivo. By functional delivery, it is meant that the RNAi polynucleotide is delivered to the cell and has the expected biological activity, sequence-specific inhibition of gene expression. Many molecules, including polynucleotides, administered to the vasculature of a mammal are normally cleared from the body by the liver. Clearance of a polynucleotide by the liver wherein the polynucleotide is degraded or otherwise processed for removal from the body and wherein the polynucleotide does not cause sequence-specific inhibition of gene expression is not considered functional delivery.

The RNAi polynucleotide conjugate is formed by covalently linking the RNAi polynucleotide to the polynucleotide targeting moiety. The polynucleotide is synthesized or modified such that it contains a reactive group A. The targeting moiety is also synthesized or modified such that it contains a reactive group B. Reactive groups A and B are chosen such that they can be linked via a covalent linkage using methods known in the art.

The targeting moiety may be linked to the 3' or the 5' end of the RNAi polynucleotide. For siRNA polynucleotides, the targeting moiety may be linked to either the sense strand or the antisense strand, though the sense strand is preferred.

In one embodiment, the polynucleotide targeting moiety consists of a hydrophobic group More specifically, the polynucleotide targeting moiety consists of a hydrophobic group having at least 20 carbon atoms. Hydrophobic groups used as polynucleotide targeting moieties are herein referred to as hydrophobic targeting moieties. Exemplary suitable hydrophobic groups may be selected from the group comprising: cholesterol, dicholesterol, tocopherol, ditocopherol, didecyl, didodecyl, dioctadecyl, didodecyl, dioctadecyl, isoprenoid, and choleamide. Hydrophobic groups having 6 or fewer carbon atoms are not effective as polynucleotide targeting moieties, while hydrophobic groups having 8 to 18 carbon atoms provide increasing polynucleotide delivery with increasing size of the hydrophobic group (i.e. increasing number of carbon atoms). Attachment of a hydrophobic targeting moiety to an RNAi polynucleotide does not provide efficient functional in vivo delivery of the RNAi polynucleotide in the absence of co-administration of the delivery polymer. While siRNA-cholesterol conjugates have been reported by others to deliver siRNA (siRNA-cholesterol) to liver cells in vivo, in the absence of any additional delivery vehicle, high concentrations of siRNA are required and delivery efficacy is poor. When combined with the delivery polymers described herein, delivery of the polynucleotide is greatly improved. By providing the siRNA-cholesterol together with a delivery polymer of the invention, efficacy of siRNA-cholesterol is increased about 100 fold.

Hydrophobic groups useful as polynucleotide targeting moieties may be selected from the group consisting of: alkyl group, alkenyl group, alkynyl group, aryl group, aralkyl group, aralkenyl group, and aralkynyl group, each of which may be linear, branched, or cyclic, cholesterol, cholesterol derivative, sterol, steroid, and steroid derivative. Hydrophobic targeting moieties are preferably hydrocarbons, containing only carbon and hydrogen atoms. However, substitutions or heteroatoms which maintain hydrophobicity, for example fluorine, may be permitted. The hydrophobic targeting moiety may be attached to the 3' or 5' end of the RNAi polynucleotide using methods known in the art. For RNAi polynucleotides having 2 strands, such as siRNA, the hydrophobic group may be attached to either strand.

In another embodiment, the polynucleotide targeting moiety comprises a galactose cluster (galactose cluster targeting moiety). As used herein, a galactose cluster comprises a molecule having two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C-1 carbon. The asialoglycoprotein receptor (ASGPr) is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945). Mulivalency is required to achieve nM affinity. The attachment of a single galactose derivative having affinity for the asialoglycoprotein receptor does not enable functional delivery of the RNAi polynucleotide to hepatocytes in vivo when co-administered with the delivery polymer.

galactose

A galactose cluster contains three galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No.

5,885,968; Biessen et al. J. Med. Chem. 1995 Vol. 39 p. 1538-1546). A preferred flexible hydrophilic spacer is a PEG spacer. A preferred PEG spacer is a PEG$_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide. Attachment of the branch point to the RNAi polynucleotide may occur through a linker or spacer. A preferred spacer is a flexible hydrophilic spacer. A preferred flexible hydrophilic spacer is a PEG spacer. A preferred PEG spacer is a PEG$_3$ spacer (three ethylene units). The galactose cluster may be attached to the 3' or 5' end of the RNAi polynucleotide using methods known in the art. For RNAi polynucleotides having 2 strands, such as siRNA, the galactose cluster may be attached to either strand.

A preferred galactose derivative is an N-acetyl-galactosamine (GalNAc). Other saccharides having affinity for the asialoglycoprotein receptor may be selected from the list comprising: galactose, galactosamine, N-formylgalactosamine, N-acetylgalactosamine, N-propionyl-galactosamine, N-n-butanoylgalactosamine, and N-iso-butanoyl-galactos-amine. The affinities of numerous galactose derivatives for the asialoglycoprotein receptor have been studied (see for example: Iobst, S. T. and Drickamer, K. *J.B.C.* 1996, 271, 6686) or are readily determined using methods typical in the art.

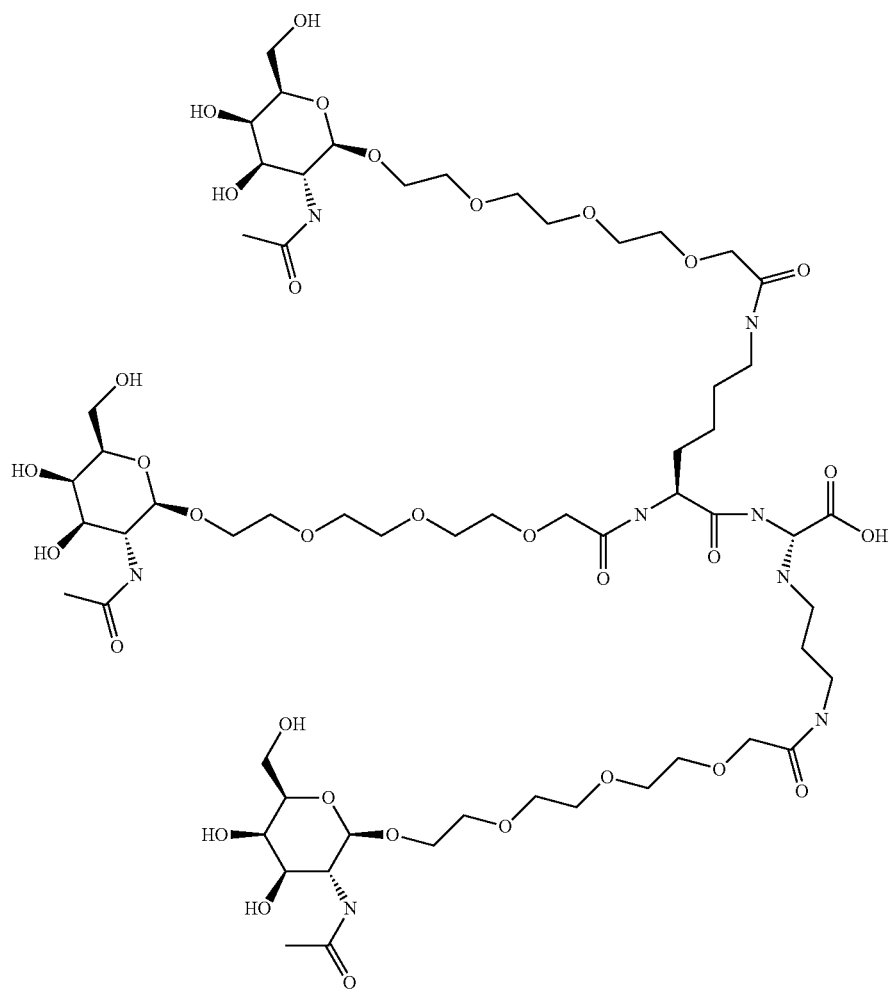

One Embodiment of a Galactose Cluster

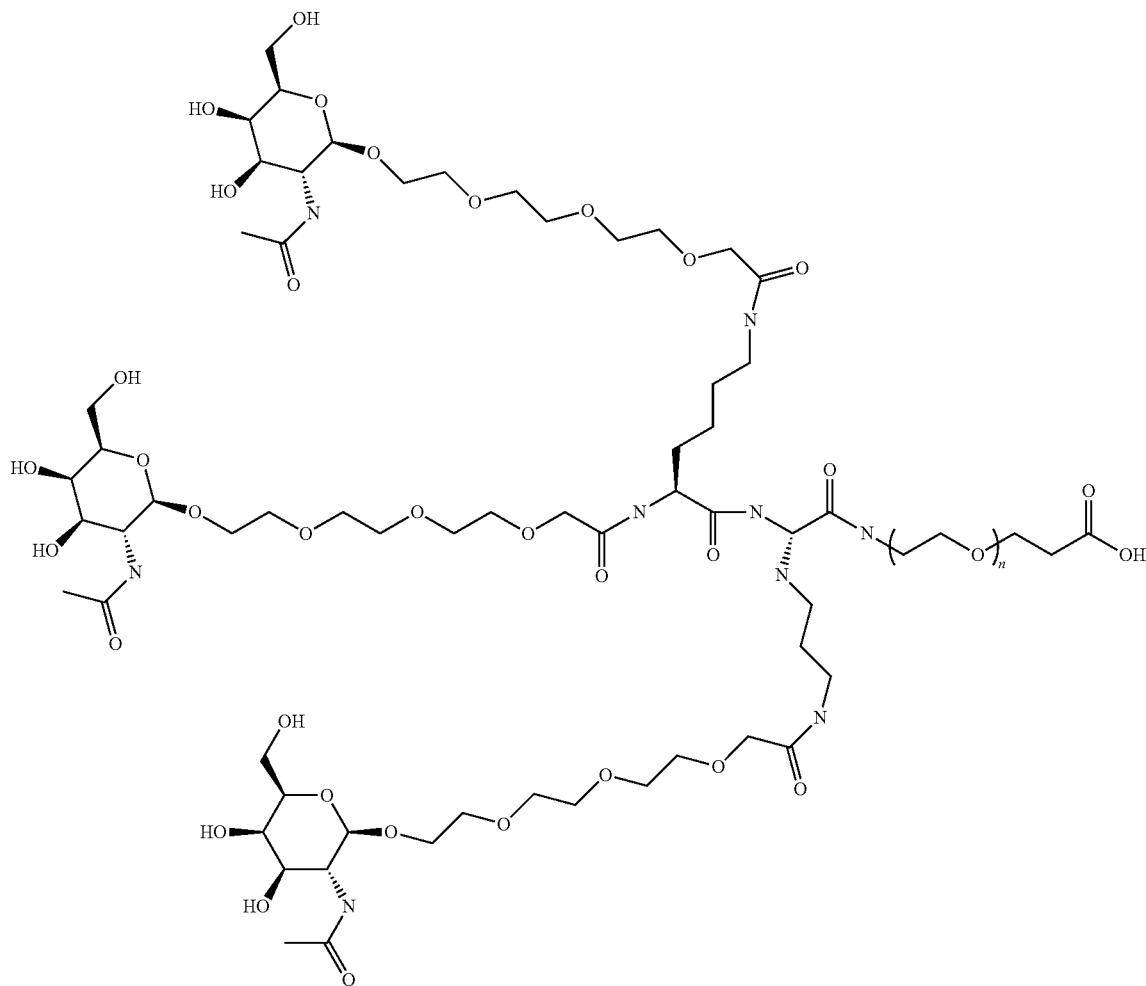

Galactose Cluster with PEG Spacer Between Branch Point and Nucleic Acid

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5'-end, the 3'-end, or both the 5' and 3' ends. The cap moiety can be, but is not limited to, an inverted deoxy abasic moiety, an inverted deoxy thymidine moiety, a thymidine moiety, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term complementarity refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

The RNAi polynucleotide-targeting moiety conjugate is co-administered with the delivery polymer. By co-administered it is meant that the RNAi polynucleotide and the delivery polymer are administered to the mammal such that both are present in the mammal at the same time. The RNAi polynucleotide-targeting moiety conjugate and the delivery polymer may be administered simultaneously or they may be delivered sequentially. For simultaneous administration, they may be mixed prior to administration. For sequential administration, either the RNAi polynucleotide-targeting moiety conjugate or the delivery polymer may be administered first.

For RNAi polynucleotide-hydrophobic targeting moiety conjugates, the RNAi conjugate may be administered up to 30 minutes prior to administration of the delivery polymer. Also for RNAi polynucleotide-hydrophobic targeting moiety conjugates, the delivery polymer may be administered up to two hours prior to administration of the RNAi conjugate.

For RNAi polynucleotide-galactose cluster targeting moiety conjugates, the RNAi conjugate may be administered up to 15 minutes prior to administration of the delivery polymer. Also for RNAi polynucleotide-galactose cluster targeting moiety conjugates, the delivery polymer may be administered up to 15 minutes prior to administration of the RNAi conjugate.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is one of the most important target tissues for gene therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by polynucleotide-based liver therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

The amount (dose) of delivery polymer and RNAi-polynucleotide-conjugate that is to be administered can be determined empirically. We have shown effective knockdown of gene expression using 0.1-10 mg/kg animal weight of siRNA-conjugate and 5-60 mg/kg animal weight delivery polymer. A preferred amount in mice is 0.25-2.5 mg/kg siRNA-conjugate and 10-40 mg/kg delivery polymer. More preferably, about 12.5-20 mg/kg delivery polymer is administered. The amount of RNAi polynucleotide-conjugate is easily increased because it is typically not toxic in larger doses.

As used herein, in vivo means that which takes place inside an organism and more specifically to a process performed in or on the living tissue of a whole, living multicellular organism (animal), such as a mammal, as opposed to a partial or dead one.

EXAMPLES

Polymer Syntheses

Example 1

Poly(Vinyl Ether) Random Copolymers

A. Vinyl Ether Monomers for Incorporation of Amine-Containing Monomers

2-Vinyloxy Ethyl Phthalimide was prepared via reacting 2-chloroethyl vinyl ether (25 g, 0.24 mol; CAS #110-75-8) and potassium phthalimide (25 g, 0.135 mol; CAS #1074-82-4) in 100° C. N,N-Dimethylformamide (DMF, 75 ml) using tetra n-butyl ammonium bromide (0.5 g; CAS #1643-19-2) as the phase transfer catalyst. This solution was heated for 6 h and then crashed out in water and filtered. This solid was then recrystallized twice from methanol to give white crystals.

B. Synthesis of Water-Soluble, Amphipathic, Membrane Active Poly(Vinyl Ether) Polyamine Terpolymers X mol % amine-protected vinylether (e.g., 2-Vinyloxy Ethyl Phthalimide) is added to an oven dried round bottom flask under a blanket of nitrogen in anhydrous dichloromethane. To this solution Y mol % lower hydrophobic group (e.g., propyl, butyl) vinylether and optionally Z mol % higher hydrophobic group (e.g., dodecyl, octadecyl) vinylether are added (FIG. 1). The solution is placed in a −50 to −78° C. bath, and the 2-vinyloxy ethyl phthalimide is allowed to precipitate. To this solution 10 mol % $BF_3 \cdot (OCH_2CH_3)_2$ is added and the reaction is allowed to proceed for 2-3 h at −50 to −78° C. Polymerization is terminated by addition of ammonium hydroxide in methanol solution. The polymer is brought to dryness under reduced pressure and then brought up in 1,4-dioxane/methanol (2/1). 20 mol eq. of hydrazine per phthalimide is added to remove the protecting group from the amine. The solution is refluxed for 3 h and then brought to dryness under reduced pressure. The resulting solid is dissolved in 0.5 mol/L HCl and refluxed for 15-min to form the hydrochloride salt of the polymer, diluted with distilled water, and refluxed for an additional hour. The solution is then neutralized with NaOH, cooled to room temperature (RT), transferred to molecular cellulose tubing, dialyzed against distilled water, and lyophilized. The polymer can be further purified using size exclusion or other chromatography. The molecular weight of the polymers is estimated using columns according to standard procedures, including analytical size-exclusion chromatography and size-exclusion chromatography with multi-angle light scattering (SEC-MALS).

C. Synthesis of DW1360

An amine/butyl/octadecyl poly(vinyl ether) terpolymer, was synthesized from 2-vinyloxy ethyl phthalimide (5 g, 23.02 mmol), butyl vinylether (0.665 g, 6.58 mmol), and octadecyl vinylether (0.488 g, 1.64 mmol) monomers. 2-vinyloxy ethyl phthalimide was added to a 200 mL oven dried round bottom flask containing a magnetic stir bar under a blanket of Argon in 36 mL anhydrous dichloromethane. To this solution was added butyl vinyl ether and n-octadecyl vinyl ether. The monomers were fully dissolved at room temperature (RT) to obtain a clear, homogenous solution. The reaction vessel containing the clear solution was then placed into a −50° C. bath generated by addition of dry ice to a 1:1 solution of ACS grade denatured alcohol and ethylene glycol and a visible precipitation of phthalimide monomer was allowed to form. After cooling for about 1.5 min, $BF_3 \cdot (OCH_2CH_3)_2$ (0.058 g, 0.411 mmol) was added to initiate the polymerization reaction. The phthalimide monomer dissolved upon initiation of polymerization. The reaction was allowed to proceed for 3 h at −50° C. The polymerization was stopped by the addition of 5 mL of 1% ammonium hydroxide in methanol. The solvents were then removed by rotary evaporation.

The polymer was then dissolved in 30 mL of 1,4-dioxane/methanol (2/1). To this solution was added hydrazine (0.147 g, 46 mmol) and the mixture was heated to reflux for 3 h. The solvents were then removed by rotary evaporation and the resulting solid was then brought up in 20 mL of 0.5 mol/L HCl and refluxed for 15 minutes, diluted with 20 mL distilled water, and refluxed for an additional hour. This solution was then neutralized with NaOH, cooled to RT, transferred to 3,500 molecular weight cellulose tubing, dialyzed for 24 h (2×20 L) against distilled water, and lyophilized.

While polymers containing the indicated vinyl ether monomers are described, the invention is not limited to these particular monomers.

D. Synthesis of Water-Soluble, Amphipathic, Membrane Active Poly(Acrylate) Polyamine Terpolymers Poly(acrylate) and poly(methylacrylate) heteropolymers may be synthesized using the general free radical reaction scheme (as used herein a poly(methacrylate)polyamine is a subgenus of the genus poly(acrylate)polyamine):

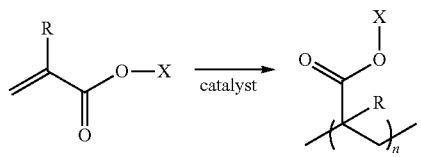

wherein R is independently a hydrogen or methyl group and X represents the desired monomer pendent groups present in the polymer at the desired ratios.

For polymer syntheses, suitable monomers include, but are not limited to:

BOC-protected amine-containing monomers (M):

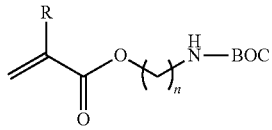

wherein n=1-4 and removal of the BOC protecting group yields a primary amine.

Lower Hydrophobic Group Monomers (N):

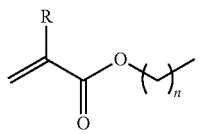

wherein n=1-5 and one or more carbons may be unsaturated.

Higher Hydrophobic Group Monomers (O):

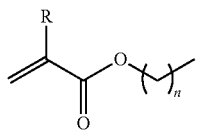

wherein n=8-24 and one or more carbons may be unsaturated.

Using the above monomers, membrane active heteropolymers can be synthesized with the following compositions: M can be 50-90 mol %; N can be 10-50 mol %; O can be 0-10 mol %.

E. Synthesis of Water-Soluble, Amphipathic, Membrane Active Poly(Acrylate)Polyamine Terpolymers

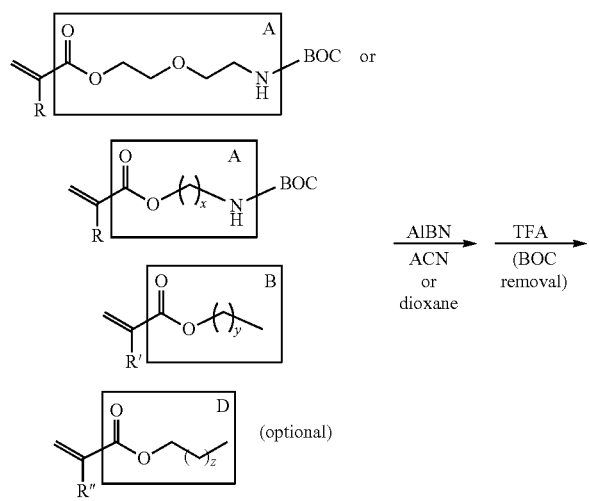

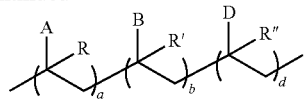

R, R', and R" are independently hydrogen or methyl
x=2, 3, or 4
y=0, 1, 2, 3, 4, or 5 [methyl (C1)-hexyl (C6)]
z=integer≥8 [decyl (C10) or greater]
a, b, and d are integers selected such that the polymer has the desired ratio of monomers as described above.

X mol % amine-protected acrylate monomer, Y mol % lower hydrophobic group acrylate monomer, and optionally Z mol % higher hydrophobic group acrylate monomer are added to a reaction tube equipped with a stir bar. An appropriate solvent (e.g., acetonitrile or dioxane) is added, followed by an appropriate catalyst (e.g., AIBN), and the reaction mixture is purged with $N_2$. The reaction tubes are then capped and transferred to an oil bath and heated (e.g., 60° C.) for sufficient time to allow polymerization (e.g., 3 h). The crude polymer may be purified by appropriate means, including but not limited to dialysis, column chromatography, and precipitation, prior to removal of the BOC protecting groups. The BOC protecting groups are removed by reaction with 2M HCl in glacial acetic acid. Removal of the BOC protecting groups yield polymer primary amines and a water soluble membrane active poly(acrylate)polyamine. The polymer may then be purified by appropriate means, including dialysis, column chromatography, and precipitation.

Synthesis of (Ant 40911-3 23-28, Ant 40911-35-2).

2,2'-Azobis(2-methylpropionitrile) (AIBN, radical initiator), acetonitrile, and dioxane were purchased from Sigma Aldrich. Acrylate and methacrylate monomers were filtered to remove inhibitors. 3-(BOC-amino)1-propanol (TCI) was reacted with acryloyl chloride (CAS 814-68-6) to produce BOC-amino propyl acrylate (BAPA).

BAPA

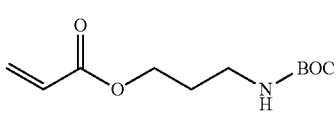

In a 2 L round-bottom flask equipped with a stir bar, 2-(2-aminoethoxy)ethanol (21.1 g, 202.9 mmol) was dissolved in 350 mL dichloromethane. In a separate 1 L flask, BOC anhydride (36.6 g, 169.1 mmol) was dissolved in 660 mL dichloromethane. The 2 L round-bottom flask was fitted with an addition funnel and BOC anhydride solution was added to the flask over 6 h. The reaction was left to stir overnight. In a 2 L separatory funnel, the product was washed with 300 ml each of 10% citric acid, 10% $K_2CO_3$, sat. $NaHCO_3$, and sat. NaCl. The product, BOC protected 2-(2-aminoethoxy)ethanol, was dried over $Na_2SO_4$, gravity filtered, and DCM was evaporated using rotary evaporation and high vacuum.

In a 500 ml round bottom flask equipped with a stir bar and flushed with argon, BOC protected 2-(2-aminoethoxy)ethanol (27.836 g, 135.8 mmol) was added, followed by 240 mL anhydrous dichloromethane. Diisopropylethyl amine (35.5 ml, 203.7 mmol) was added, and the system was placed in a dry ice/acetone bath. Acryloyl Chloride (12.1 ml, 149.4 mmol) was diluted using 10 ml of dichloromethane, and added drop-wise to the argon flushed system. The system was kept under argon and left to come to room temperature and stirred overnight. The product was washed with 100 mL each of dH$_2$O, 10% citric acid, 10% K$_2$CO$_3$, sat. NaHCO$_3$, and saturated NaCl. The product, BOC-amino ethyl ethoxy acrylate (BAEEA), was dried over Na$_2$SO$_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAEEA, was obtained with 74% yield. BAEEA was stored in the freezer.

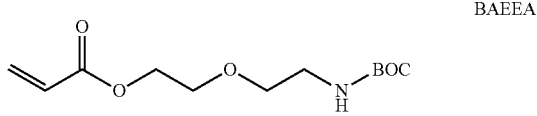 [SMILES: C=CC(=O)OCCOCCNC(=O)OC(C)(C)C]

BAEEA

Polymer 40911-3 23-28:

70% BAPA, 25% butyl methacrylate (CAS 97-88-1), 5% octadecyl methacrylate (CAS 4813-57-4), (3% AIBN catalyst) mole feed ratio (0.0139 total mol). BAPA (9.739 mmol) (A), butyl methacrylate (3.478 mmol) (B), and octadecyl methacrylate (0.6957 mmol) (D) were added to a 20 mL reaction tube equipped with a stir bar. Acetonitrile (16 ml) was added, followed by AIBN (0.4174 mmol). The above steps were repeated in order to have two reactions run in tandem. The reaction mixture was purged with N$_2$ for 30 min. The reaction tubes were then capped and transferred to an oil bath and heated at 60° C. for 3 h. The tubes were removed and the contents were combined. The crude polymer was precipitated into deionized water, and reacted with neat trifluoroacetic acid (40 ml) for 1.5 h to remove the BOC protecting groups and produce the primary amines and a water soluble membrane active poly(acrylate)polyamine. 200 mL deionized H$_2$O (dH$_2$O) were added to the reaction, the solution was transferred to 3500 MW cutoff cellulose tubing, dialyzed against high salt for 24 h, then against dH$_2$O for 18 h. The contents were evaporated to dryness, dissolved in 100 mL dH$_2$O and lyophilized. The dried polymer was dissolved in 50% MeOH/100 mM ammonium formate/0.2% formic acid solution at 25 mg/ml. Three injections of crude polymer solution (250 mg, 10 ml) were purified on S-200 sephacryl media using an XK50/30 cm column used at a flow rate of 5.0 ml/min. The column was packed and used according to the manufacturer's instructions. (GE Healthcare, instructions 56-1130-82 Al, 52-2086-00 AK). Polymer elution was detected using a Shimadzu RID-10A refractive index collector. Fractions from 23 min to 28 min were collected and combined for each run. The solvent was evaporated and the purified polymer was lyophilized twice.

Polymer Ant 40911-35-2:

80% BAEEA, 15% butyl methacrylate, 5% octadecyl acrylate, (3% AIBN catalyst) mole feed ratio (0.013913 total mol). BAEEA (A) (11.13 mmol), butyl methacrylate (B) (2.086 mmol), and octadecyl acrylate (D) (0.6957 mmol) were added to a 20 mL reaction tube equipped with a stir bar. Dioxane (16 ml) was added, followed by AIBN (0.4174 mmol). The above steps were repeated in order to have two reactions run in tandem. The reaction mixture was purged with N$_2$ for 30 min. The reaction tubes were then capped and transferred to an oil bath and heated at 60° C. for 3 h. The tubes were removed and the contents were combined. Dioxane was evaporated through rotary evaporation and high vacuum and the crude polymer was dissolved in 89.8% dichloromethane/10% tetrahydrofuran/0.2% triethylamine solution at 70 mg/ml. Three injections of crude polymer solution (700 mg, 10 ml) were purified on a Jordi gel divinyl benzene 10$^4$ Å column (internal diameter: 22 mm, length: 500 mm) used at a flow rate of 5.0 ml/min. Polymer elution was detected using a Shimadzu RID-10A refractive index collector. Fractions from 15.07 min-17.13 min were collected and combined. The solvent was evaporated through rotary evaporation.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5µ 7.8×300 Mixed Bed LS DVB column. A molecular weight of 172,000 and a PDI of 1.26 were obtained.

The purified BOC-protected polymer was reacted with neat trifluoroacetic acid (7 ml) for 1.5 h (or 2 M HCl in glacial acetic acid for 0.5 h) to remove the BOC protecting groups and produce the amines. 40 mL dH$_2$O were added to the reaction, the solution was transferred to 3500 MW cutoff cellulose tubing, dialyzed against high salt for 24 hr, then against dH$_2$O for 18 h. The contents were evaporated to dryness, then dissolved in 20-30 mL dH$_2$O and lyophilized twice. The polymer solution was stored at 2-8° C.

The number of carbon atoms linking the amine to the backbone of the polymer and whether or not the linker is branched, affects the pKa of the amine and steric effects near the amine. For example, for the above polymers, ethyl amine has a pKa of about 8.1, propyl amine has a pKa of about 9.3, and pentyl amine has a pKa of about 10.2. The pKa of the amine or steric effects near the amine affect the lability of masking groups attached to the amine. For reversible attachment of a maleic anhydride to an amine, a higher pKa of the amine results is a slower rate of release of an anhydride from the amine. Also, increased steric hindrance near the amine, such as with an isopropyl linker, may increase the pKa of the amine.

Polymer Lau 41305-38-17-19:

80% BAPA, 20% ethyl methacrylate (CAS 97-63-2), (3% AIBN catalyst) mole feed ratio (0.0105 total mol). BAPA (A) (8.40 mmol) and ethyl methacrylate (B) (2.10 mmol) were added to a 15 mL reaction tube equipped with a stir bar. Acetonitrile (11.5 ml) was added followed by AIBN (0.315 mmol). The above steps were repeated in order to have two reactions run in tandem. The reaction mixture was purged with N$_2$ for 30 min. The reaction tubes were then capped and transferred to an oil bath and heated at 60° C. for 3 h. The tubes were removed and the contents were combined. Acetonitrile was evaporated through rotary evaporation and high vacuum and the crude polymer was dissolved in 74.8% dichloromethane/25% tetrahydrofuran/0.2% triethylamine solution at 50 mg/ml. Three injections of crude polymer solution (500 mg, 10 ml) were purified on a Jordi gel fluorinated divinyl benzene 10$^4$ Å column (internal diameter: 22 mm, length: 500 mm) used at a flow rate of 5.0 ml/min. Polymer elution was detected using a Shimadzu RID-10A refractive index collector. Fractions from 17.16 min-19.18 min were collected and combined. The solvent was evaporated through rotary evaporation. The purified BOC-protected polymer was reacted with 2M HCl in glacial acetic acid (7 ml) for 1.5 h to remove the BOC protecting groups and produce the amines. 40 mL dH$_2$O were added to the reaction, the solution was transferred to 3500 MW cutoff cellulose tubing, dialyzed against high salt for 24 hr, then against dH$_2$O for 18 h. The contents were evaporated to dryness, then dissolved in 30 mL dH$_2$O and lyophilized twice.

F. Similar Polymers, Synthesized from (Protected) Amine Monomers, Lower Hydrophobic Group Monomers, and Higher Hydrophobic Group Octadecyl Groups would be Predicted to be Effective in the Practice of the Described Invention Polymer Characterization Example 2

Characterization of DW1360

A. Amphipathic Analysis 1,6-diphenyl-1,3,5-hexatriene (DPH, Invitrogen) fluorescence ($\lambda_{ex}$=350 nm; $\lambda_{em}$=452 nm) is enhanced in a hydrophobic environment. This fluorophore was used to analyze the DW1360 polymer. 0.5 µM (final concentration) DPH was added to 10 µg DW1360 in 0.5 mL 50 mM HEPES buffer, pH 8.0. The solution was then tested for DPH accumulation in a hydrophobic environment by measuring fluorescence of DPH. Increased DPH fluorescence in the presence of the conjugates indicates the formation of a hydrophobic environment by the polymer.

B. Molecular Weight.

Polymer Molecular Weights (mass) (MW) were determined on a Wyatt Dawn Heleos II run in conjunction with optilab rEX in batch mode. Polymers was brought up at varying concentrations in appropriate solvent and each was loaded onto the Wyatt system. Astra software then calculated changes in refractive index as a function of concentration (dn/dc) which was used in a Zimm plot to calculate MW. The average molecular weight determined for purified DW1360 was 4000-6000 Da. The average molecular weight for the purified acrylate polymers was about 100-120 kDa.

C. Particle Sizing and Zeta Potential.

The zeta potential of the polymers was measured using a Malvern Zetasizer nano series (Nano ZS) instrument. The zeta potential of the CDM-masked polymers varied between 0 and −30 mV and more predominantly between 0 and −20 mV. Zeta potential was measured in isotonic glucose buffered at pH 8 with residual HEPES. At pH 7, the conjugates would be expected to gain some positive charge due to protonation of some of the amines.

D. Quantification of Amine Groups in Conjugate after CDM-Reagent Modification.

DW1360 polymer was synthesized as described previously followed by treatment with 14 wt equivalents HEPES base and 7 wt equivalents of a 2:1 wt:wt mixture of CDM-NAG and CDM-PEG (average 11 units). One hour later, the amine content of the maleic anhydride derivative treated conjugate was measured by treatment with trinitrobenzene sulfonic acid (TNBS) in 100 mM NaHCO$_3$. When normalized to a conjugate that had not been maleamate modified, it was determined that the amount of modified amines was about 75% of total. This degree of modification may be varied by changing the amount of added maleic anhydride or altering the reaction conditions.

E. Liposome Lysis.

10 mg of egg phosphatidylcholine was hydrated with 1 mL of buffer containing 100 mM carboxyfluorescein (CF) and 10 mM HEPES pH 7.5. Liposomes were then be extruded through 100-nm pores polycarbonate filters (Nucleopore, Pleasanton, Calif.). Unentrapped CF was removed by size exclusion chromatography using Sepharose 4B-200 eluting with 10 mM HEPES at pH 8 and 0.1 mol/L NaCl. A 200 µL aliquot of the CF-loaded liposomes were added to 1.8 mL of isotonic buffer. Fluorescence ($\lambda_{ex}$=488, $\lambda_{em}$=540) was measured 30 min after addition of 0.25 µg of polymers to vesicle suspensions. At the end of each experiment, vesicles were disrupted by the addition of 40 µl of a 1% Triton X-100 solution to determine maximal lysis.

Polymer Masking Agents

Example 3

Masking Agents

A. Synthesis of 2-Propionic-3-Methylmaleic Anhydride Masking Agent Precursor (Carboxydimethylmaleic Anhydride or CDM)

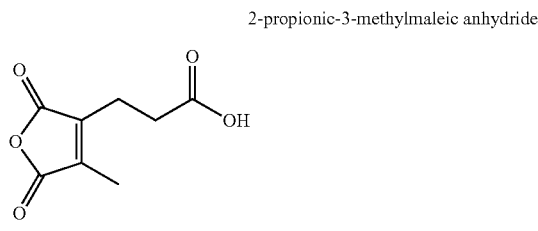

2-propionic-3-methylmaleic anhydride

To a suspension of sodium hydride (0.58 g, 25 mmol) in 50 mL anhydrous tetrahydrofuran was added triethyl-2-phosphonopropionate (7.1 g, 30 mmol). After evolution of hydrogen gas had stopped, dimethyl-2-oxoglutarate (3.5 g, 20 mmol) in 10 mL anhydrous tetrahydrofuran was added and stirred for 30 min. 10 mL water was then added, and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 g (82% yield) of pure triester. The 2-propionic-3-methylmaleic anhydride was then formed by dissolving of this triester into 50 mL of a 50/50 mixture of water and ethanol containing 4.5 g (5 equivalents) of potassium hydroxide. This solution was heated to reflux for 1 h. The ethanol was then removed by rotary evaporation and the solution was acidified to pH 2 with hydrochloric acid. This aqueous solution was then extracted with 200 mL ethyl acetate, isolated, dried with magnesium sulfate, and concentrated to a white solid. This solid was then recrystallized from dichloromethane and hexane to yield 2 g (80% yield) of 2-propionic-3-methylmaleic anhydride.

Thioesters, esters, and amides may be synthesized from CDM by conversion of CDM to its acid chloride with oxalyl chloride followed by the addition of a thiol, ester, or amine and pyridine. CDM and its derivatives are readily modified, by methods standard in the art, with targeting ligands, steric stabilizers, charged groups, and other reactive groups. The resultant molecules can be used to reversibly modify amines.

Masking agents were synthesized through modification of CDM to produce preferably charge neutral agents:

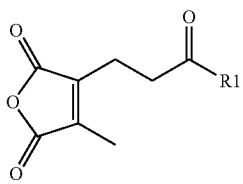

wherein R1 comprises an ASGPr targeting ligand or steric stabilizer (e.g. PEG).

B. Masking Agent Containing an ASGPr Targeting Group.

The most widely-studied hepatocyte targeting ligands are based on galactose, which is bound by the asialoglycoprotein receptor (ASGPr) on hepatocytes. Attachment of galactose or a galactose derivative has been shown to facilitate hepatocyte targeting of a few highly water soluble, uncharged polymers, including: the oligosaccharide chitosan, a polystyrene derivative, and a polyacrylamide HPMA. ASGPr targeting groups are readily generated using lactose, a galactose-glucose disaccharide, via modification of the glucose residue. Lactobionic acid (LBA, a lactose derivative in which the glucose has been oxidized to gluconic acid) is readily incorporated into a maleic anhydride derivative using standard amide coupling techniques.

ably, PEG containing 10-14 ethylene units are attached to the di-substituted maleic anhydride. The PEG may be of variable length and have a mean length of 5-20 or 10-14 ethylene units. Alternatively, the PEG may be monodisperse, uniform or discrete; having, for example, exactly 11 or 13 ethylene units.

CDM-NAG

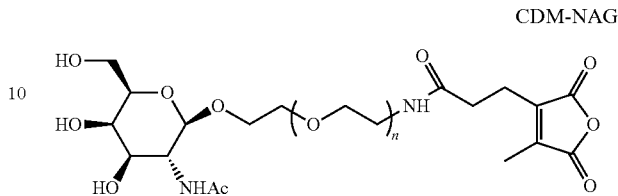

As shown above, a PEG spacer may be positioned between the anhydride group and the ASGPr targeting group. A preferred PEG spacer contains 1-10 ethylene units.

CDM-NAG with alkyl spacer

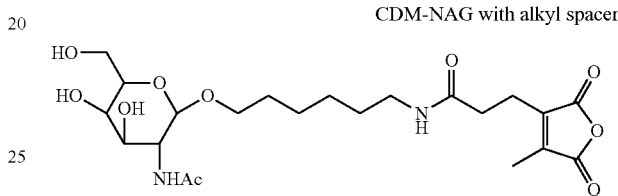

CDM-lactose

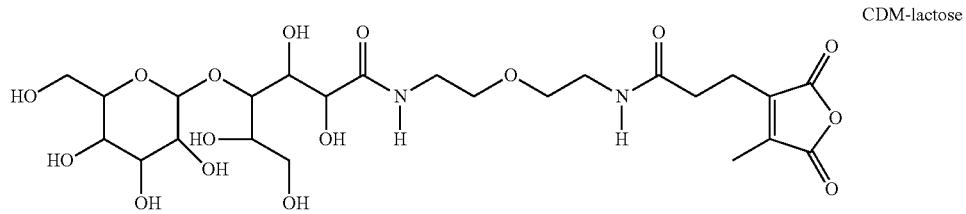 [SMILES: CC1=C(CCC(=O)NCCOCCNC(=O)C(O)C(O)C(OC2OC(CO)C(O)C(O)C2O)C(O)CO)C(=O)OC1=O]

C. Steric Stabilizer CDM-PEG and Targeting Group CDM-NAG (N-Acetyl Galactosamine) Syntheses To a solution of CDM (300 mg, 0.16 mmol) in 50 mL methylene chloride was added oxalyl chloride (2 g, 10 wt. eq.) and dimethylformamide (5 µl). The reaction was allowed to proceed overnight, after which the excess oxalyl chloride and methylene chloride were removed by rotary evaporation to yield the CDM acid chloride. The acid chloride was dissolved in 1 mL of methylene chloride. To this solution was added 1.1 molar equivalents polyethylene glycol monomethyl ether (MW average 550) for CDM-PEG or (aminoethoxy)ethoxy-2-(acetylamino)-2-deoxy-β-D-galactopyranoside (i.e. amino bisethoxy-ethyl NAG) for CDM-NAG, and pyridine (200 µl, 1.5 eq) in 10 mL of methylene chloride. The solution was then stirred 1.5 h. The solvent was then removed and the resulting solid was dissolved into 5 mL of water and purified using reverse-phase HPLC using a 0.1% TFA water/acetonitrile gradient.

CDM-PEG

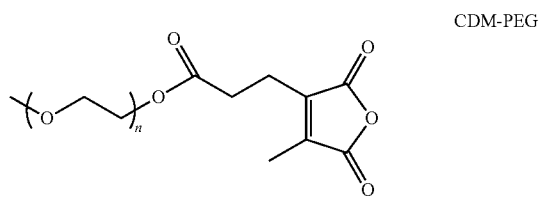

Preferably, PEG containing from 5 to 20 ethylene units are attached to the di-substituted maleic anhydride. More prefer- Reversible Polymer Modification Example 4

Reversible Modification/Masking of Membrane Active Polyamine; i.e., Modification of Membrane Active Polymer with CDM-NAG or a Mixture of CDM-NAG Plus CDM-PEG To a solution of xmg membrane active polyamine (e.g. DW1360 described above) in isotonic glucose was added 14× mg of HEPES free base followed by either 7× mg CDM-NAG or a mixture of 2.3× mg CDM-NAG and 4.6× mg CDM-PEG, for a total of 7× disubstituted maleic anhydride masking agent. The solution was then incubated for at least 30 min at RT prior to animal administration. Reaction of CDM-NAG or CDM-PEG with the polyamine yielded:

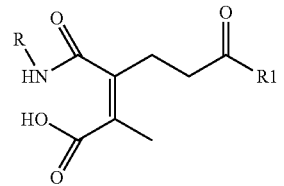

wherein R is the polymer and R1 comprises a ASGPr targeting moiety or steric stabilizer. The anhydride carboxyl produced in the reaction between the anhydride and the polymer amine exhibits ~1/20$^{th}$ of the expected charge (Rozema et al. Bioconjugate Chemistry 2003). Therefore, the membrane active polymer is effectively neutralized rather than being converted to a highly negatively charged polyanion.

siRNA-conjugate

Example 5

RNAi Polynucleotide-Targeting Moiety Conjugates

A. siRNA-Hydrophobe Conjugate.

Various hydrophobic groups were covalently linked to 3' or 5' ends of siRNA molecules using techniques standard in the art.

B. siRNA-GalNAc Cluster Conjugate.

The GalNAc cluster was made by attachment of three GalNAc PEG$_3$ groups to the amines on a di-lysine branch point. The carboxyl group on the di-lysine is then available for covalent attachment to the RNAi polynucleotide, such as an siRNA.

In Vivo siRNA Delivery

Example 6

Administration of RNAi polynucleotides in vivo, and delivery to hepatocytes. RNAi polynucleotide conjugates and masked polymers were synthesized as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). RNAi polynucleotide conjugates and masked polymers were synthesized as described above. Mice were injected with 0.2 mL solution of delivery polymer and 0.2 mL siRNA conjugates into the tail vein. For simultaneous injection of polymer and siRNA, the siRNA-conjugate was added to modified polymer prior to injection and the entire amount, 0.4 ml, was injected. The composition was soluble and nonaggregating in physiological conditions. For injections in which polymer and siRNA are injected separately, polymer was injected in 0.2 mL of formulation solution and siRNA was injected in 0.2 mL of isotonic glucose. Solutions were injected by infusion into the tail vein. Injection into other vessels, e.g. retro-orbital injection, were equally effective.

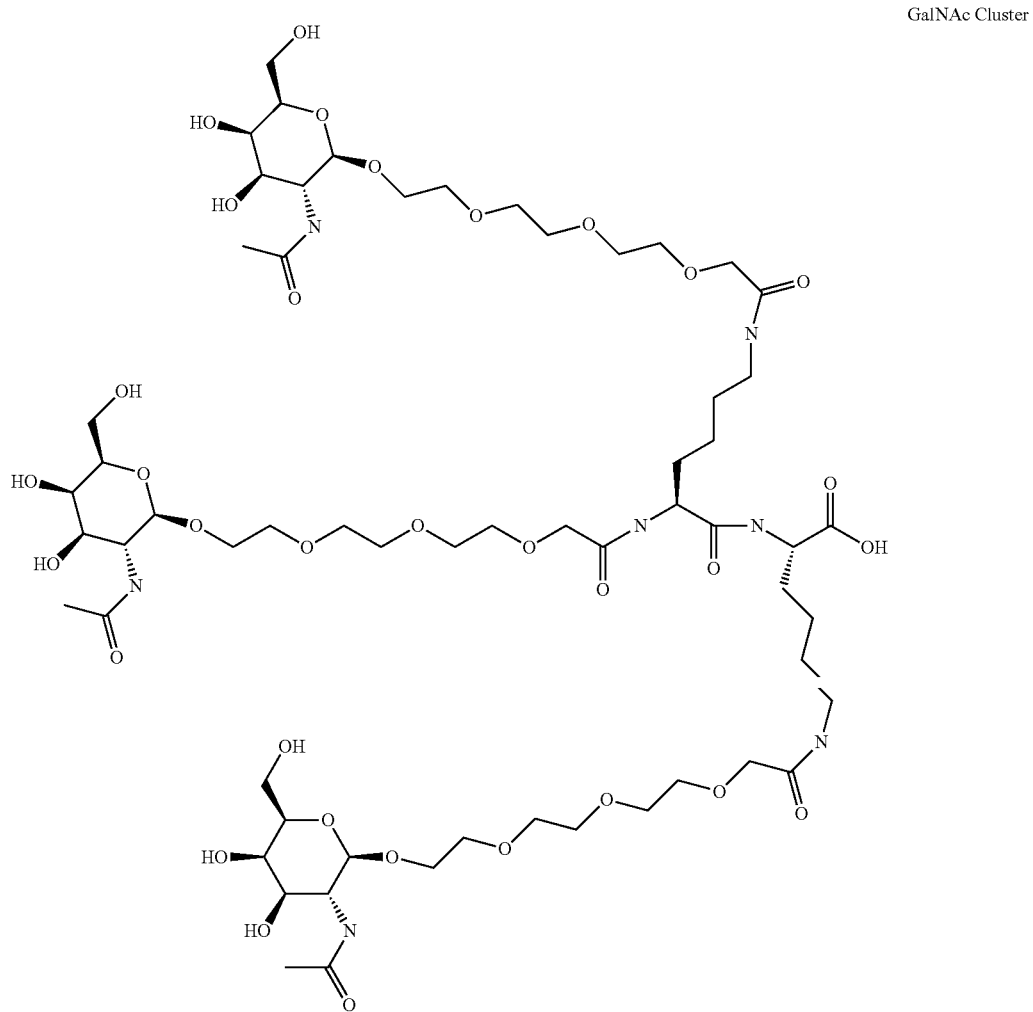 [SMILES: CC(=O)N[C@H]1[C@H](OCCOCCOCCOCC(=O)NCCCC[C@H](NC(=O)[C@H](CCCCNC(=O)COCCOCCOCCO[C@@H]2O[C@H](CO)[C@H](O)[C@H](O)[C@H]2NC(C)=O)NC(=O)COCCOCCOCCO[C@@H]2O[C@H](CO)[C@H](O)[C@H](O)[C@H]2NC(C)=O)C(=O)O)O[C@H](CO)[C@H](O)[C@@H]1O]

GalNAc Cluster

Serum ApoB Levels Determination.

Mice were fasted for 4 h (16 h for rats) before serum collection by submandibular bleeding. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) Activity Measurements.

Plasma samples from mice were prepared by collecting blood (9 volumes) by submandibular bleeding into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 7

Delivery of siRNA to Hepatocytes In Vivo Using siRNA-Hydrophobe Conjugates Co-Administered with Masked DW1360 Delivery Polymer siRNA and delivery polymer were prepared and administered as described above using the indicated doses of siRNA and polymer.

A. RNAi Polynucleotide Delivery to Hepatocytes In Vivo.

Figure 2:
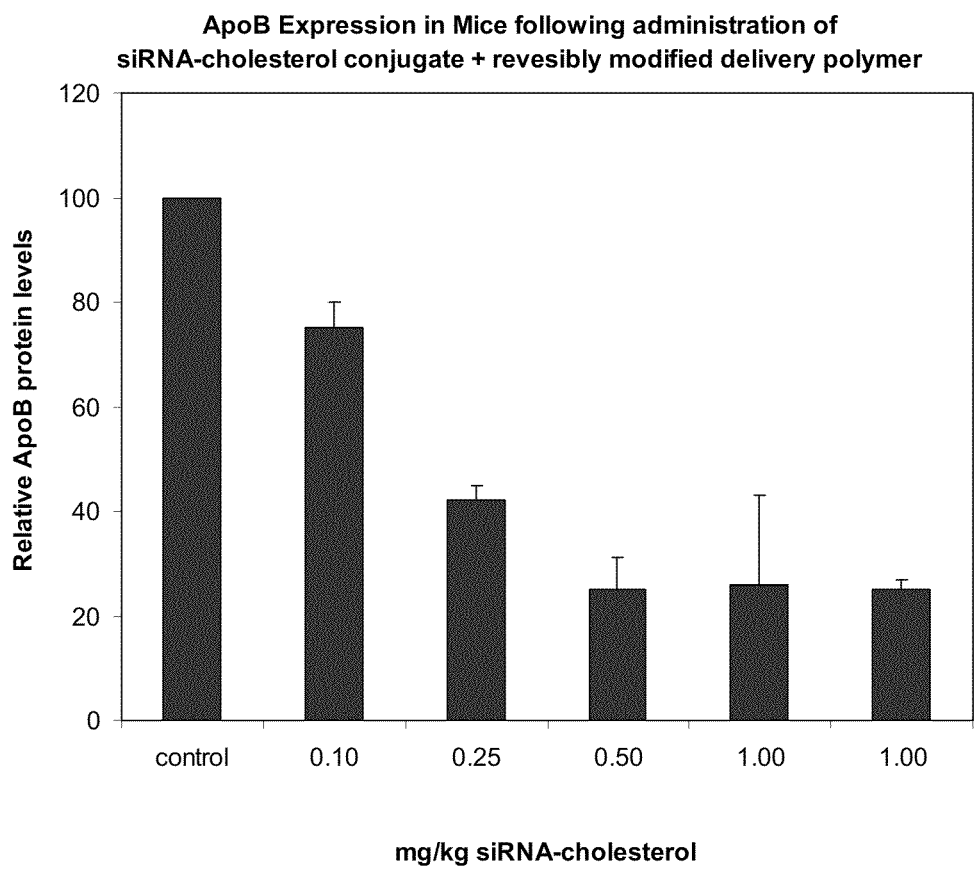
FIG. 2. Graph illustrating the effect of siRNA-cholesterol conjugate dose on gene knockdown.

Co-administration of siRNA-cholesterol conjugate and masked DW1360 delivery polymer resulted in decreased serum ApoB protein levels, indicating delivery of the siRNA to hepatocytes and inhibition of apoB gene expression. Efficient delivery required both the delivery polymer and cholesterol conjugation to the RNAi polynucleotide (Table 1, FIG. 2). No significant knockdown was observed with up to 5 mg/kg unconjugated siRNA. Further, the hydrophobic group could be attached to either the 5' or 3' end of the siRNA.

TABLE 1

Knockdown of target gene in vivo following injection of siRNA-hydrophobe conjugate plus DW1360 delivery polymer, effect of siRNA-conjugate dose.

| siRNA | siRNA dose (mg/kg) | Polymer dose (mg/kg) | Relative % ApoB [a, b] |
|---|---|---|---|
| 5' cholesterol apoB | 0.1 | 20 | 75 ± 5 |
| | 0.25 | 20 | 42 ± 3 |
| | 0.5 | 20 | 25 ± 6 |
| | 1 | 20 | 26 ± 17 |
| 3' cholesterol apoB | 1 | 20 | 25 ± 2 |
| | 5 | 0 | 102 ± 33 |
| unconjugated siRNA | 0.5 | 16 | 87 ± 4 |
| | 5 | 16 | 71 ± 20 |

[a] Percent knockdown relative to control group (n = 3) injected with isotonic glucose solution.
[b] ICR mice B. Effect of Hydrophobic Group Size on RNAi Polynucleotide Delivery to Hepatocytes.

Figure 3:
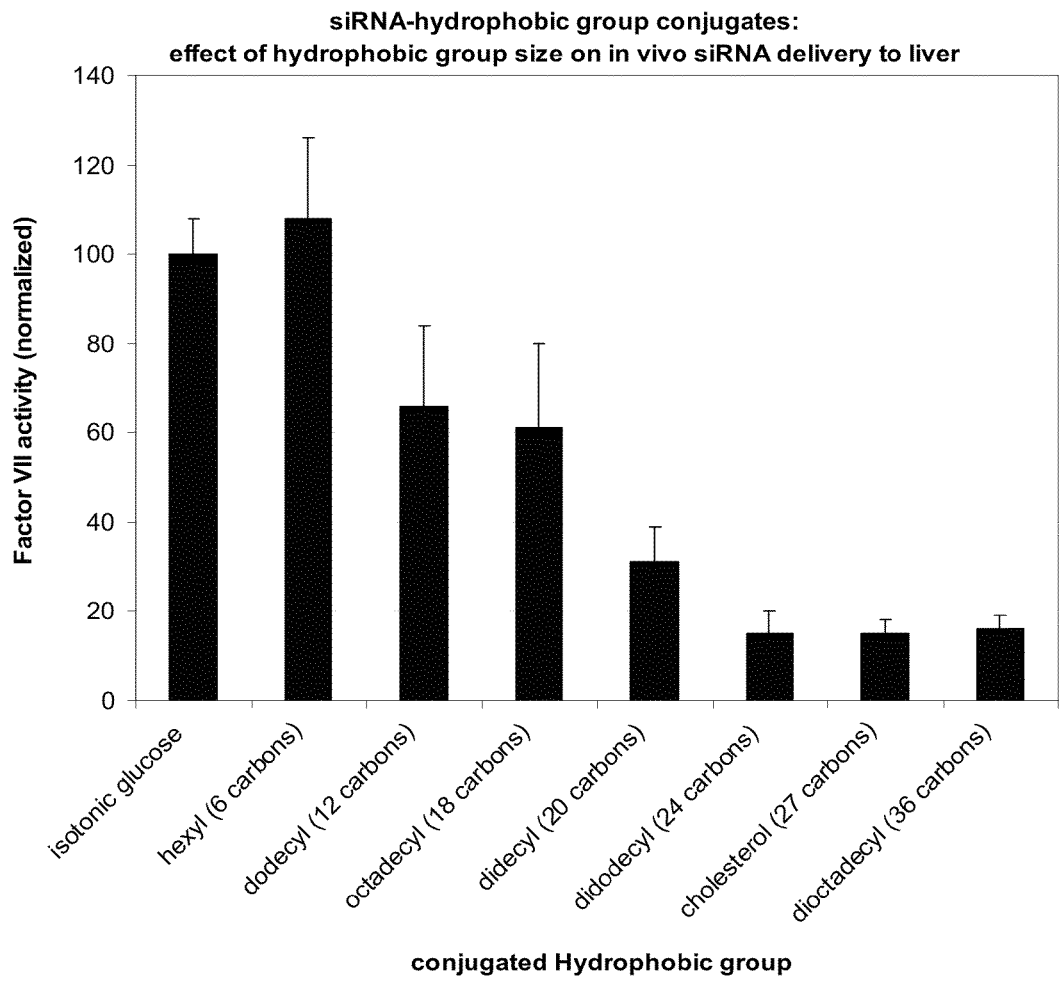
FIG. 3. Graph illustrating the effect of hydrophobe size on siRNA-hydrophobe conjugate targeting to liver.

Efficient delivery of siRNA to hepatocytes, using co-administration with DW1360 delivery polymer required that the siRNA be conjugated to a hydrophobic group having about 20 or more carbon atoms (Table 2, FIG. 3). siRNA-hydrophobe conjugates having hydrophobic targeting moieties with fewer than 20 carbon atoms exhibited progressively less efficient functional delivery. Hydrophobe targeting moieties having six (6) or fewer carbons were ineffective. Delivery efficiency was not significantly improved by increasing the size of the hydrophobe targeting moiety beyond 20 carbon atoms.

TABLE 2

Knockdown of target gene in vivo following injection of siRNA-hydrophobe conjugate plus DW1360 delivery polymer - effect of hydrophobic group size.

| siRNA | Carbon atoms [b] | siRNA dose (mg/kg) | Polymer dose (mg/kg) | Relative % Factor VII [a, c] |
|---|---|---|---|---|
| 5'-hexyl fVII | 6 | 2.5 | 12.5 | 108 ± 18 |
| 5'-dodecyl fVII | 12 | 2.5 | 12.5 | 66 ± 18 |
| 5'-octadecyl fVII | 18 | 2.5 | 12.5 | 61 ± 19 |
| 5'-(decyl)$_2$ fVII | 20 | 2.5 | 12.5 | 31 ± 8 |
| 5'-(dodecyl)$_2$ fVII | 24 | 2.5 | 12.5 | 15 ± 5 |
| 5'-cholesterol fVII | 27 | 2.5 | 12.5 | 15 ± 3 |
| 5'-(octadecyl)$_2$ fVII | 36 | 2.5 | 12.5 | 16 ± 3 |

[a] Percent knockdown relative to control group (n = 3) injected with isotonic glucose solution.
[b] number of carbon atoms in the hydrophobic group conjugated to the siRNA
[c] C57BL/6 mice C. Effect of siRNA Dose on siRNA-Hydrophobe Conjugate Delivery to Hepatocytes.

Figure 4:
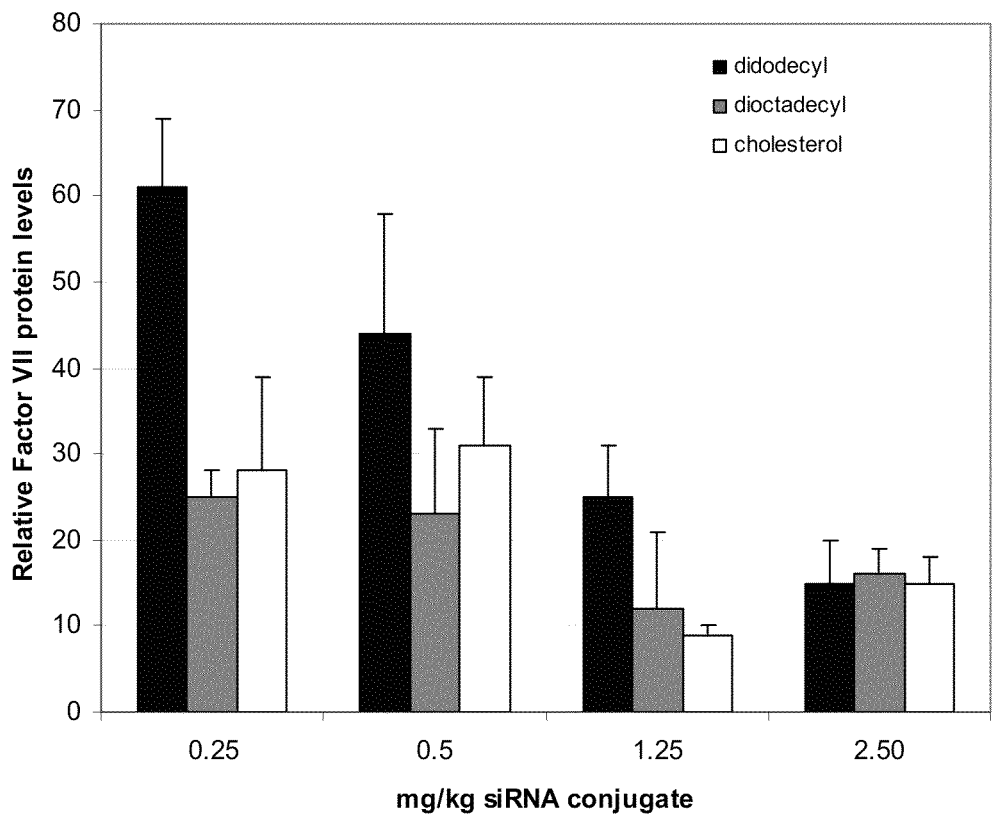
FIG. 4. Graph illustrating the effect of siRNA-hydrophobe conjugate dose on gene knockdown for several hydrophobic groups.

Knockdown of target gene expression in vivo is dependent on siRNA dose. For treatment of mice, administration of more than 1.25 mg/kg siRNA dose did not improve target gene knockdown in vivo (Table 3, FIG. 4). Dosage as low as 0.25 mg/kg did however provide significant knockdown of target gene expression in mice when co-administered with delivery polymer.

TABLE 3

Knockdown of target gene in vivo following injection of siRNA-hydrophobe conjugate plus DW1360 delivery polymer-effect of siRNA dose.

| siRNA | siRNA dose (mg/kg) | Polymer dose (mg/kg) | Relative % Factor VII [a, b] |
|---|---|---|---|
| 5'-(dodecyl)$_2$ fVII | 2.5 | 12.5 | 15 ± 5 |
| | 1.25 | 12.5 | 25 ± 6 |
| | 0.5 | 12.5 | 44 ± 14 |
| | 0.25 | 12.5 | 61 ± 8 |
| 5'-(octadecyl)$_2$ fVII | 2.5 | 12.5 | 16 ± 3 |
| | 1.25 | 12.5 | 12 ± 9 |
| | 0.5 | 12.5 | 23 ± 10 |
| | 0.25 | 12.5 | 25 ± 3 |
| 5'-cholesterol fVII | 2.5 | 12.5 | 15 ± 3 |
| | 1.25 | 12.5 | 9 ± 1 |
| | 0.5 | 12.5 | 31 ± 8 |
| | 0.25 | 12.5 | 28 ± 11 |

[a] Percent knockdown relative to control group (n = 3) injected with isotonic glucose solution.
[b] C57BL/6 mice D. Knockdown of Target Gene Expression In Vivo is Dependent on Delivery Polymer Dose.

Figure 5:
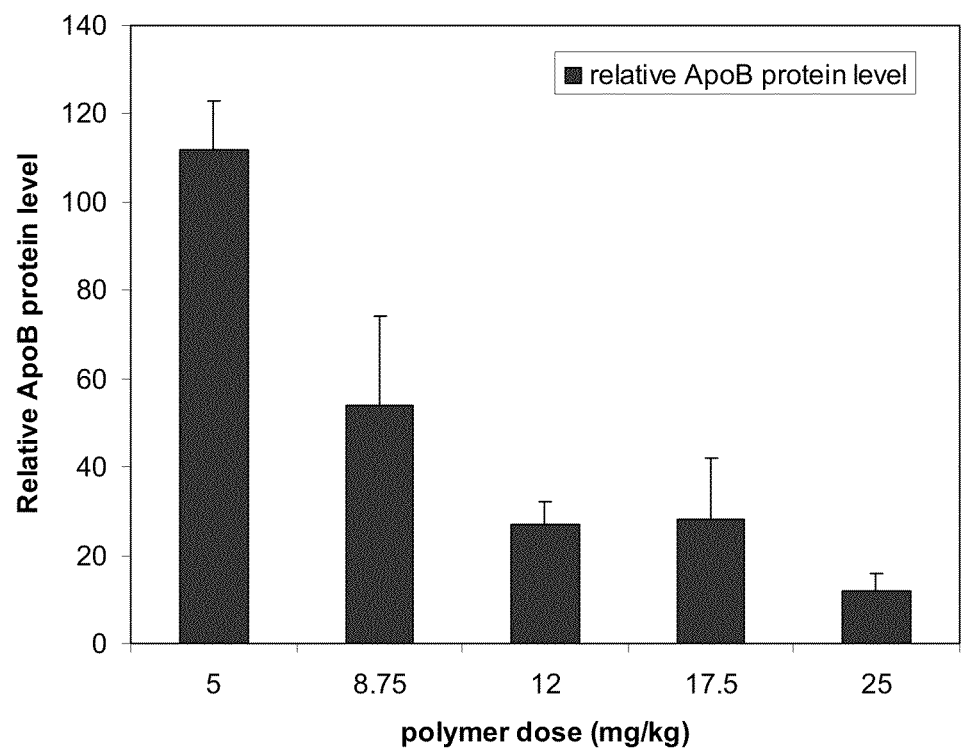
FIG. 5. Graph illustrating the effect of delivery polymer dose on siRNA-hydrophobe conjugate delivery to liver.

For treatment of mice, administration of about 12.5 mg/kg delivery polymer provided maximal or near maximal RNAi-polynucleotide delivery as evidenced by target gene inhibition (Table 4, FIG. 5). Knockdown of target gene is affected by polymer dose. Excess siRNA-conjugate did not improve target gene knockdown in the absence of sufficient polymer for delivery.

TABLE 4

Knockdown of target gene in vivo following injection of siRNA-hydrophobe conjugate plus DW1360 delivery polymer-effect of delivery polymer dose.

| siRNA | siRNA dose (mg/kg) | Polymer dose (mg/kg) | Relative % ApoB [a] |
|---|---|---|---|
| 3'-cholesterol apoB | 1 | 5 | 112 ± 11 [b] |
| | 1 | 8.75 | 54 ± 20 [b] |
| | 1 | 12.5 | 27 ± 5 [b] |
| | 1 | 17.5 | 28 ± 14 [b] |
| | 1 | 25 | 12 ± 4 [b] |
| | 1 | 3.75 | 91 ± 21 [c] |
| | 1 | 7 | 59 ± 30 [c] |
| | 1 | 12.5 | 38 ± 19 [c] |
| | 10 | 3.75 | 74 ± 13 [c] |
| | 10 | 7 | 71 ± 24 [c] |

[a] Percent knockdown relative to control group (n = 3) injected with isotonic glucose solution.
[b] ICR mice
[c] C57BL/6 mice

E. Sequential Administration.

The RNAi polynucleotide-hydrophobe targeting moiety conjugate and delivery polymer may be administered to the animal sequentially. For RNAi polynucleotide-hydrophobic targeting moiety conjugates, the RNAi conjugate may be administered up to 30 minutes prior to administration of the delivery polymer. Also for RNAi polynucleotide-hydrophobic targeting moiety conjugates, the delivery polymer may be administered up to two hours prior to administration of the RNAi conjugate (Table 5).

TABLE 5

Knockdown of target gene in vivo following injection of siRNA-hydrophobe conjugate plus DW1360 delivery polymer-effect of sequential administration of siRNA and polymer.

| siRNA | First injection | Interval | Second injection | Relative % ApoB [a] |
|---|---|---|---|---|
| 5'-cholesterol apoB | 0.5 mg/kg siRNA | 15 min | 12.5 mg/kg polymer | 25 ± 5 |
| | | 30 min | | 35 ± 13 |
| | | 120 min | | 90 ± 20 |
| | 12.5 mg/kg polymer | 120 min | 0.5 mg/kg siRNA | 20 ± 5 |
| 3'-cholesterol apoB | 0.5 mg/kg siRNA | 0 min | 12.5 mg/kg polymer | 27 ± 11 |
| | | 15 min | | 25 ± 9 |
| | | 30 min | | 34 ± 12 |
| | 12.5 mg/kg polymer | 15 min | 0.5 mg/kg siRNA | 41 ± 6 |
| | | 30 min | | 41 ± 15 |

[a] Percent protein relative to control group (n = 3) injected with isotonic glucose solution.

F. Membrane Active Poly(Acrylate) Delivery Polymers.

Reversibly masked amphipathic membrane active poly(acrylate)polyamines function as effective delivery polymers. Poly(acrylate)polymers were prepared as described above and co-administered with siRNA-cholesterol conjugates in mice as described for DW1360 delivery polymers. The poly(acrylate) delivery polymers were effective in facilitating delivery of siRNA to hepatocytes in vivo as indicated by reduced serum ApoB (Table 6). Efficient delivery required both the delivery polymer and cholesterol conjugation to the RNAi polynucleotide.

TABLE 6

Knockdown of target gene in vivo following injection of siRNA-hydrophobe conjugate plus masked poly(acrylate) delivery polymers.

| Poly(acrylate) polymer | siRNA | siRNA dose (mg/kg) | Polymer dose (mg/kg) | Relative % ApoB |
|---|---|---|---|---|
| Ant 40911-3 23-38 | 5' cholesterol apoB | 0.5 | 15 | 14 ± 4 |
| Ant 40911-35-2 | 5' cholesterol apoB | 0.5 | 20 | 23 ± 10 |

G. Delivery of RNAi Polynucleotide-Hydrophobe Conjugate to Liver was not Dependent on Either the LDL-Receptor or the Lipoprotein Receptor-Related Protein.

Co-administration of Factor VII siRNA-cholesterol conjugate and masked DW1360 delivery polymer resulted in decreased in serum Factor VII protein levels in LDL-Receptor knockout mice and Lipoprotein Receptor-Related Protein/LDL-Receptor double knockout mice. Therefore, siRNA-cholesterol is targeted to hepatocytes by means other than LDL particles, LDL-Receptor or Lipoprotein Receptor-Related Protein (Table 7).

TABLE 7

Knockdown of target gene in vivo following injection of siRNA-cholesterol conjugate plus DW1360 delivery polymer; effect of LDL receptor and Lipoprotein Receptor-Related Protein on siRNA delivery.

| siRNA | siRNA dose (μg) | Polymer dose [a] (μg) | Polymer modification | Relative % Factor VII [a] |
|---|---|---|---|---|
| LDL Receptor knockout mice | | | | |
| cholesterol-siRNA Factor VII | 0 | 0 | | 100 ± 18 |
| | 20 | 400 | NAG + PEG | 35 ± 18 |
| | 20 | 400 | NAG | 26 ± 7 |
| | 20 | 400 | PEG | 99 ± 9 |
| Lipoprotein Receptor-Related Protein/ LDL-Receptor double knockout mice | | | | |
| cholesterol-siRNA Factor VII | 0 | 0 | | 100 ± 20 |
| | 20 | 400 | NAG + PEG | 11 ± 4 |
| | 20 | 400 | NAG | 26 ± 9 |
| | 20 | 400 | PEG | 88 ± 26 |

[a] relative % protein

H. Lyophilized Poly(Vinyl Ether) Samples.

To test whether the delivery polymer could be lyophilized for improved storage and transport, delivery polymer in solution was frozen and placed in high vacuum on a lyophilizer. After 16 h, the sample was a crystalline powder that was then redissolved by addition of deionized water. To the redissolved polymer sample was added siRNA (5' cholesterol apoB), and the sample was injected. Lyophilization showed no detrimental effects on the delivery polymer.

Galactose Cluster Targeted siRNA

Example 8

Delivery of siRNA to hepatocytes in vivo using siRNA-galactose cluster conjugates co-administered with masked DW1360 delivery polymer. siRNA and delivery polymer were prepared and administered as described above using the indicated doses of siRNA and polymer.

A. Co-Administration of siRNA-Galactose Cluster Conjugate and Masked DW1360 Delivery Polymer.

Co-administration of siRNA-galactose cluster conjugate and masked DW1360 delivery polymer resulted in decreased serum ApoB protein levels, indicating delivery of the siRNA to hepatocytes and inhibition of apoB gene expression. Efficient delivery required both the delivery polymer and galactose cluster conjugation to the RNAi polynucleotide (Table 8). No significant knockdown was observed with up to 5 mg/kg unconjugated siRNA. As with the hydrophobe conjugate siRNA above, onset of maximum inhibition is obtained with about 12.5 mg/kg delivery polymer dose. No target gene knockdown was observed in the absence of co-administered delivery polymer. The galactose cluster-siRNA conjugate exhibited no activity by itself.

TABLE 8

Knockdown of target gene in vivo following injection of siRNA-GalNAc cluster conjugate plus delivery polymer, effect of polymer dose.

| siRNA | siRNA dose [a] (mg/kg) | Polymer dose [a] (mg/kg) | Relative % ApoB [b] |
|---|---|---|---|
| 5'GalNAc cluster apoB | 0.5 | 10 | 48 ± 9 |
|  | 0.5 | 20 | 26 ± 12 |
|  | 0.5 | 40 | 15 ± 6 |
|  | 0.5 | 60 | 18 ± 10 |
| unconjugated siRNA | 0.5 | 16 | 87 ± 4 |

[a] mg siRNA or polymer per kilogram animal weight
[b] relative % protein

B. siRNA-Galactose Cluster Vs. siRNA-Galactose Monomer.

Functional delivery of siRNA to hepatocytes in vivo when co-administered with delivery polymer required a tri-antennary galactose targeting moiety conjugated to the RNAi interference polynucleotide. No target gene knockdown was observed when a single galactose molecule was conjugated to the siRNA (Table 9). The GalNPr (N-propionyl galactosamine) galactose derivative is known to have a higher affinity for the ASGPr than the GalNAc (N-acetyl-galactosamine) galactose derivative, further indicating the necessity of the triantennary galactose cluster for efficient delivery.

TABLE 9

Knockdown of target gene in vivo following injection of siRNA-GalNAc cluster conjugate plus delivery polymer; trivalent vs. monovalent galactose RNA conjugate.

| siRNA | Ligand | siRNA dose [a] (mg/kg) | Polymer dose [a] (mg/kg) | Relative % protein [b] |
|---|---|---|---|---|
| apoB | 5'GalNPr monomer [c] | 0.25 | 12.5 | 100 ± 7 |
|  | 5'GalNAc cluster [d] | 0.25 | 12.5 | 56 ± 11 |

[a] mg siRNA or polymer per kilogram animal weight
[b] relative % protein
[c] N-Propionyl Galactosamine monomer
[d] N-Acetyl Galactosamine cluster (trimer)

C. Effect of Modification of Polymer with Galactose Derivative, PEG, or Galactose Derivative Plus PEG.

siRNA-galactose cluster and delivery polymer were prepared as described above except as follows: the delivery polymer was either masked with N-acetylgalactosamine alone, PEG alone, or N-acetylgalactosamine plus PEG. siRNA and delivery polymer were then administered to mice as described above. Blood samples were then collected from mice and assayed to determine ApoB levels. Both galactose and PEG were required for optimal delivery. By modifying the membrane active polymer with both galactose and PEG, only half of the siRNA dose was required to achieve the same effect and polymer modified with galactose alone. Modification of polymer with PEG alone resulted in decreased siRNA delivery compared to polymer modified with galactose alone or with galactose plus PEG.

TABLE 10

Knockdown of target gene in vivo following injection of siRNA-GalNAc cluster conjugate plus delivery polymer; effect of polymer modification.

| siRNA | siRNA dose [a] (mg/kg) | Polymer dose [a] (mg/kg) | Polymer modification | Relative % ApoB [b] |
|---|---|---|---|---|
| 5'GalNAc cluster apoB | 0.5 | 20 | CDM-NAG + CDM-PEG | 26 ± 12 |
|  | 1 | 20 | CDM-NAG | 23 ± 10 |
|  | 1 | 20 | CDM-PEG | 45 ± 10 |

[a] mg siRNA or polymer per kilogram animal weight
[b] relative % protein

D. Time Course of Sequence Specific Gene Knockdown Following Co-Administration of siRNA-Targeting Moiety Conjugate and Delivery Polymer.

siRNA and delivery polymer were prepared as and administered to mice as described above. Blood samples were then collected from mice at the indicated times and assayed to determine ApoB levels. ApoB levels were observed to gradually decrease until they reached 3% of control lever after 72 h. Thus, maximum target gene knockdown may occur after about three (3) days. This delay in onset of maximum decrease in protein levels may reflect the time required to clear or degrade ApoB protein rather than the time required for maximum RNAi polynucleotide delivery or for gene knockdown.

TABLE 11

Knockdown of target gene in vivo following injection of siRNA-GalNAc cluster conjugate plus delivery polymer; time course of target gene knockdown.

| siRNA | siRNA dose [a] (mg/kg) | Polymer dose [a] (mg/kg) | Hours post injection | Relative % protein [b] |
|---|---|---|---|---|
| 5'GalNAc cluster apoB | 1 | 20 | 5 | 134 ± 15 |
|  |  |  | 24 | 35 ± 3 |
|  |  |  | 48 | 12 ± 2 |
|  |  |  | 72 | 3 ± 1 |

[a] mg siRNA or polymer per kilogram animal weight
[b] relative % protein

E. Sequential Injection of siRNA-Galactose Cluster Conjugate and Delivery Polymer.

The indicated amounts of siRNA-galactose cluster conjugate and delivery polymer were prepared and administered to mice as described above. Blood samples were then collected from mice and assayed to determine ApoB levels. For siRNA targeted to the liver with the galactose cluster, optimal delivery was observed with simultaneous delivery of the siRNA and delivery polymer. Significant siRNA delivery was observed when the siRNA-conjugate was administered up to 15 minutes after administration of the polymer. Only modest delivery was observed when the siRNA-conjugate was administered prior to (up to 15 minutes) the delivery polymer.

TABLE 12

Knockdown of target gene in vivo following injection of siRNA-GalNAc cluster conjugate plus delivery polymer; simultaneous administration and separate administration.

| siRNA | First injection | Interval | Second injection | Relative % apoB |
|---|---|---|---|---|
| 5'GalNAc cluster apoB | 0.25 mg/kg siRNA | 0 min | 12.5 mg/kg polymer | 28 ± 14 |
| | 12.5 mg/kg polymer | 15 min | 0.25 mg/kg siRNA | 56 ± 18 |

TABLE 12-continued

Knockdown of target gene in vivo following injection of siRNA-GalNAc cluster conjugate plus delivery polymer; simultaneous administration and separate administration.

| siRNA | First injection | Interval | Second injection | Relative % apoB |
|---|---|---|---|---|
| | 0.25 mg/kg siRNA | 15 min | 12.5 mg/kg polymer | 88 ± 14 |

F. Insertion of a PEG Linker Between the Galactose Cluster Targeting Ligand and the RNAi Polynucleotide.

siRNA-galactose cluster conjugates were either prepared inserting PEG spacers, $PEG_{19}$ or $PEG_{24}$, between the galactose cluster and the siRNA or prepared without a PEG spacer between the galactose cluster and the siRNA. The siRNA-conjugates were then co-administered with delivery polymer. Insertion of PEG spacers did not improve delivery of the siRNA to hepatocytes as determined by gene knockdown.

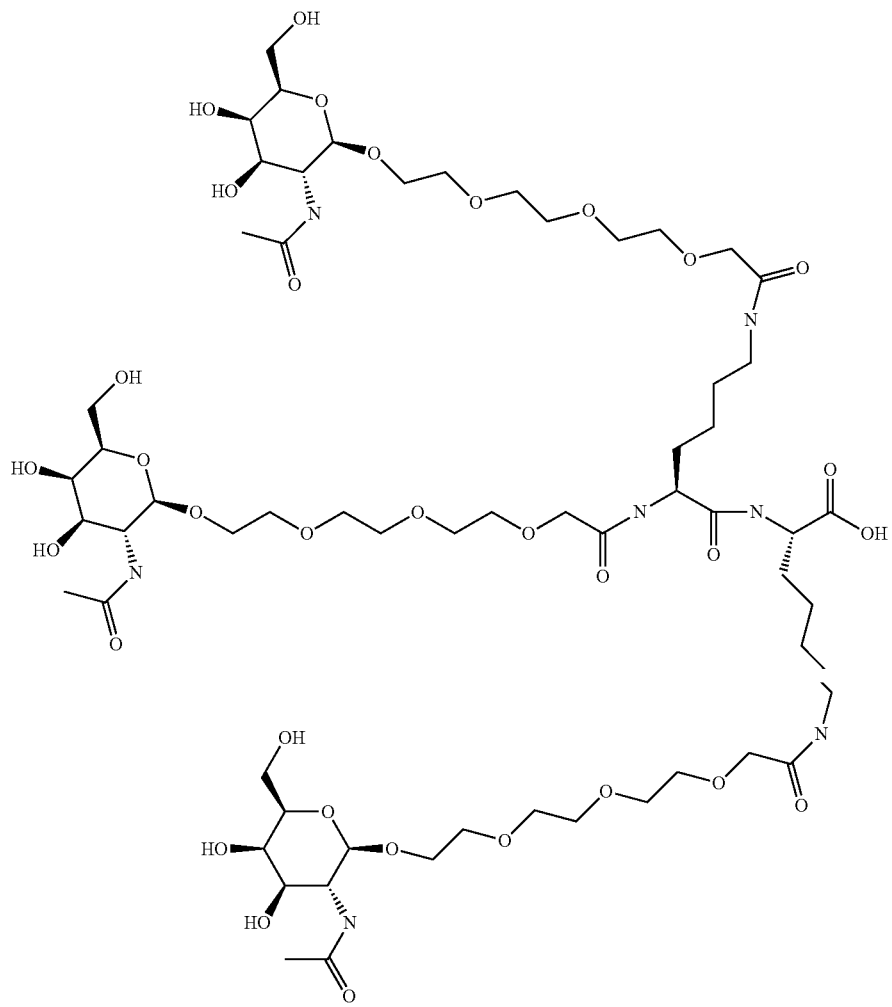

Galactose cluster without PEG spacer; targeting ligand attached to the siRNA through the carboxyl group.

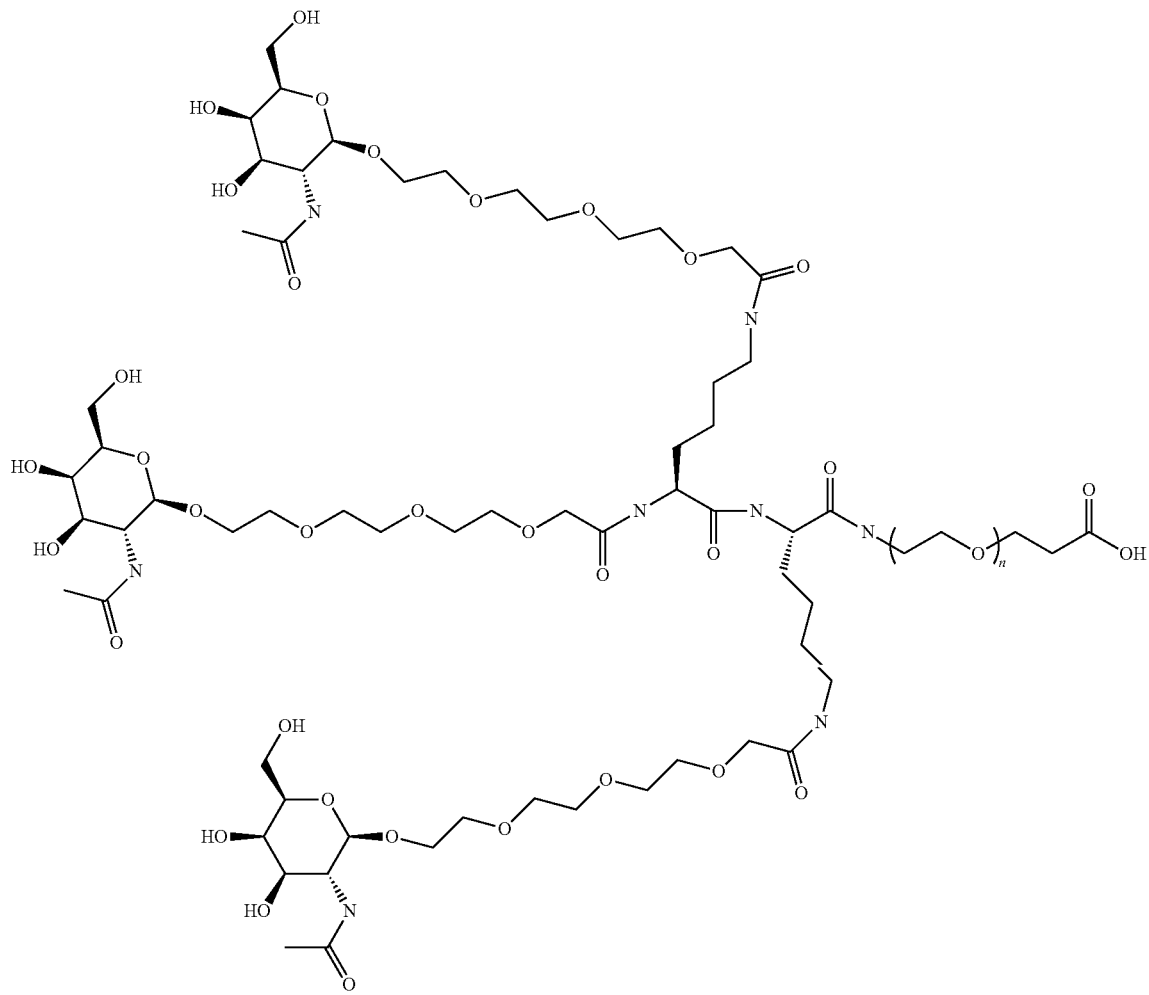

Galactose cluster with PEG spacer; targeting ligand attached to the siRNA through the carboxyl group.

TABLE 13

Knockdown of target gene in vivo following injection of siRNA-GalNAc cluster conjugate plus delivery polymer; effect of PEG linker in RNA conjugate.

| siRNA | siRNA dose[a] (mg/kg) | PEG linker | Polymer dose[a] (mg/kg) | Relative % ApoB[b] |
|---|---|---|---|---|
| 5'GalNAc cluster apoB | 0.25 | none | 12.5 | 28 ± 14 |
| 5'GalNAc cluster-PEG$_{19}$ apoB | 0.25 | PEG$_{19}$ | 12.5 | 82 ± 19 |
| 5'GalNAc cluster-PEG$_{24}$ apoB | 0.25 | PEG$_{24}$ | 12.5 | 72 ± 13 |

[a] mg siRNA or polymer per kilogram animal weight
[b] relative % protein

Example 9

Delivery of siRNA to primate hepatocytes in vivo. RNAi polynucleotide conjugates and masked polymers were synthesized as described above.

A Rhesus monkey (3.9 kg male) was injected I.V. with 7.8 mL of a solution containing 1.0 mg/ml cholesterol-siApoB and 7.5 mg/ml DW1360 modified with 7× wt ratio of 2:1 CDM-PEG:CDM-NAG, giving a final dose of 2 mg/kg cholesterol-siApoB and 15 mg/kg DW1360. Another Rhesus monkey (4.5 kg male) was injected with isotonic glucose and served as a control.

Serum ApoB Levels Determination.

Serum ApoB protein levels were monitored during the course. Primates was fasted for 4 h before serum collection. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm. The results are given in Table 14. The Rhesus monkey receiving the cholesterol-siApoB siRNA showed a decrease in serum ApoB levels over time, reaching a maximum knockdown of 76% on Day 15 after injection compared to Day −1 pre-dose levels. ApoB levels recovered to the near Day −1 pre-dose levels on Day 50. No decrease in serum ApoB levels were observed in the control animal.

TABLE 14

Serum ApoB levels normalized to Day 1.

| | Treatment | |
|---|---|---|
| Day | Isotonic glucose | chol-siRNA (ApoB) + polymer |
| 1 | 1.00 | 1 |
| 2 | 1.24 | 1.07 |
| 4 | 1.38 | 0.69 |
| 7 | 1.22 | 0.56 |
| 11 | 1.39 | 0.32 |
| 15 | 1.43 | 0.24 |
| 18 | 1.36 | 0.25 |
| 22 | 1.44 | 0.31 |
| 29 | 1.13 | 0.30 |
| 36 | 1.21 | 0.48 |

Example 10

Simultaneous knockdown of two genes. Co-administration of siRNA-cholesterol conjugates to two independent genes, apoB and factor VII, and masked DW1360 delivery polymer resulted in simultaneous inhibition of both genes. The composition was administered to mice as described above. (Table 15).

TABLE 15

Simultaneous knockdown of 2 target genes in vivo following injection of two different siRNA-hydrophobe conjugates plus 400 µg DW1360 delivery polymer.

| 3' cholesterol-apoB (µg) | 3' cholesterol-factor VII (µg) | Relative % ApoB [a] | Relative % Factor VII [a] |
|---|---|---|---|
| 0 | 0 | 100 ± 19 | 100 ± 25 |
| 20 | 0 | 12 ± 4 | 124 ± 21 |
| 0 | 20 | 81 ± 12 | 14 ± 5 |
| 20 | 20 | 10 ± 6 | 12 ± 1 |

[a] Percent knockdown relative to control group (n = 3) injected with isotonic glucose solution.

Toxicity Evaluation

Example 11

Toxicity. The potential toxicity of the delivery system was assessed by measuring serum levels of liver enzymes and cytokines. Slight elevations of ALT and AST levels were detected in mice receiving control siRNA or apoB-1 siRNA conjugates as compared to saline-treated mice 48 h after injection. However, the increased levels were not significant ($p<0.05$), and histological examination of liver sections did not reveal signs of liver toxicity. Similarly, analysis of TNF-α and IL-6 levels in serum using ELISA revealed that both were slightly elevated 6 h after injection of siRNA-polymer conjugate. The levels of both returned to baseline by 48 h. No statistically significant toxicity was measured at the minimal effective dose in mice or rats. These results indicate the targeted delivery system was well-tolerated.

Example 12

The siRNAs Had the Following Sequences

```
apoB siRNA:
                                         (SEQ ID 1)
sense     5' GGAAUCuuAuAuuuGAUCcAsA 3'

(SEQ ID 2)
antisense 5' uuGGAUcAAAuAuAAGAuUCcscsU 3' factor VII siRNA
                                         (SEQ ID 3)
sense     5' GGAUfCfAUfCfUfCfAAGUfCfUfUfACfdTdT 3'

(SEQ ID 4)
antisense 5' GUfAAGACfUfUfGAGAUfGAUfCfCfdTsdT 3' small letter = 2'-O—CH3 substitution
s = phosphorothioate linkage
f after nucleotide = 2'-F substitution
d before nucleotide = 2'-deoxy
```

Example 13

Synthesis of GalNAc Cluster

A. {2-[2-(2-Hydroxy-ethoxy)-ethoxy]-ethoxy}-acetic acid benzyl ester

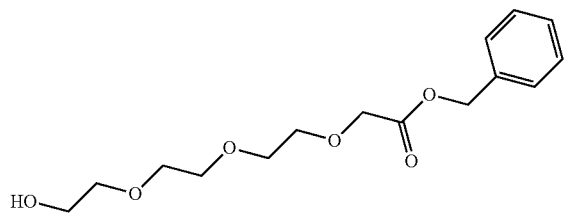 [SMILES: O=C(COCCOCCOCCO)OCc1ccccc1]

2-[2-(2-Hydroxy-ethoxy)-ethoxy]-ethanol (62.2 g, 414 mmol) was dissolved under argon in 875 mL of abs. DMF and cooled to 0° C. NaH (12.1 g, 277 mmol, 55% in mineral oil) was carefully added, the ice bath removed, and stirring continued for 1 h at 80° C. The reaction mixture was cooled to ambient temperature and treated with bromoacetic acid (18.98 g, 137 mmol) which was added via dropping funnel as a DMF-solution (20 ml). After an additional 30 min. at 75° C., bromomethyl-benzene (23.36 g, 137 mmol) was added neat and esterification allowed to proceed for 30 min. Cooling, careful pouring onto crashed ice, extraction with ethyl acetate, washing with water, drying over $Na_2SO_4$, and evaporation of all solvents followed by flash chromatography (SiO₂, ethyl acetate/heptane=8/2) yielded 6.41 g of the title compound as a yellow oil. MS (ISP): 299.2 [M+H]⁺.

B. Acetic acid (3aR,5R,6R,7R,7aR)-6-acetoxy-5-acetoxymethyl-2-methyl-5,6,7,7a-tetrahydro-3aH-pyrano[3,2-d]oxazol-7-yl ester

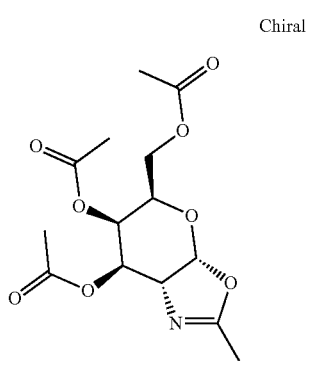 [SMILES: CC(=O)OC[C@H]1O[C@@H]2OC(C)=N[C@@H]2[C@@H](OC(C)=O)[C@H]1OC(C)=O]

Commercially available acetic acid (2S,3R,4R,5R,6R)-4,5-diacetoxy-6-acetoxymethyl-3-acetylamino-tetrahydro-pyran-2-yl ester (10.0 g, 26 mmol) was dissolved in 116 mL of abs. CH₂Cl₂ and treated with trimethylsilyl triflate (14.27 g, 64 mmol). The reaction was allowed to proceed over night at 45° C. After cooling to 0° C., triethylamine (4.88 ml, 35 mmol) was added, the mixture diluted with CH₂Cl₂ and washed with NaHCO₃-solution and water. Drying over Na₂SO₄ and evaporation of the solvent yielded 10.3 g of the title compound as brownish oil which was used without further purification for the next step. MS (ISP): 330.0 [M+H]⁺.

C. (2-{2-[2-((2R,3R,4R,5R,6R)-4,5-Diacetoxy-6-acetoxymethyl-3-acetylamino-tetrahydro-pyran-2-yloxy)-ethoxy]-ethoxy}-ethoxy)-acetic acid benzyl ester The above prepared acetic acid (3aR,5R,6R,7R,7aR)-6-acetoxy-5-acetoxymethyl-2-methyl-5,6,7,7a-tetrahydro-3aH-pyrano[3,2-d]oxazol-7-yl ester (10.3 g, 26 mmol) and {2-[2-(2-hydroxy-ethoxy)-ethoxy]-ethoxy}-acetic acid benzyl ester (8.62 g, 29 mmol) were mixed in 520 mL of CH₂Cl₂ and treated with 63 g of 4 Angstrom molecular sieves. After 1 h trimethylsilyl triflate (6.13 g, 28 mmol) was added. The reaction mixture was stirred over the weekend at ambient temperature. Triethylamine (5.21 ml, 37 mmol) was added, the molecular sieves filtered off, the filtrate diluted with CH₂Cl₂ and washed with NaHCO₃-solution and water. Drying over Na₂SO₄ and evaporation of the solvent followed by flash chromatography (SiO₂, ethyl acetate/AcOH/MeOH/water=60/3/3/2) afforded 15.7 g of the title compound as a brownish oil. MS (ISP): 626.6 [M−H]⁻.

D. (2-{2-[2-((2R,3R,4R,5R,6R)-4,5-Diacetoxy-6-acetoxymethyl-3-acetylamino-tetrahydro-pyran-2-yloxy)-ethoxy]-ethoxy}-ethoxy)-acetic acid

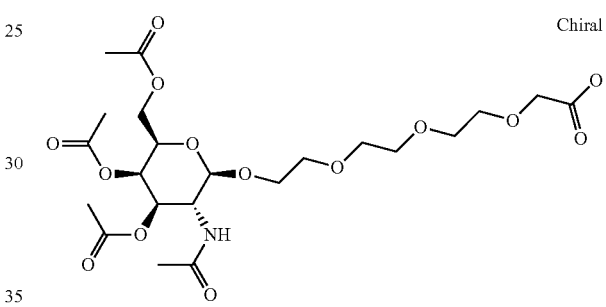

The above prepared (2-{2-[2-((2R,3R,4R,5R,6R)-4,5-diacetoxy-6-acetoxymethyl-3-acetylamino-tetrahydro-pyran-2-yloxy)-ethoxy]-ethoxy}-ethoxy)-acetic acid benzyl ester (15.7 g, 25 mmol) was dissolved in 525 mL of ethyl acetate and hydrogenated over 1.6 g of Pd/C (10%) under 1 atm. of H₂ at ambient temperature for 3 h. Filtration over Celite and evaporation of the solvent, followed by flash chromatography (SiO₂, CH₂Cl₂/MeOH=80/20) gave 6.07 g of the title compound as a brownish gum. MS (ISP): 536.5 [M−H]⁻.

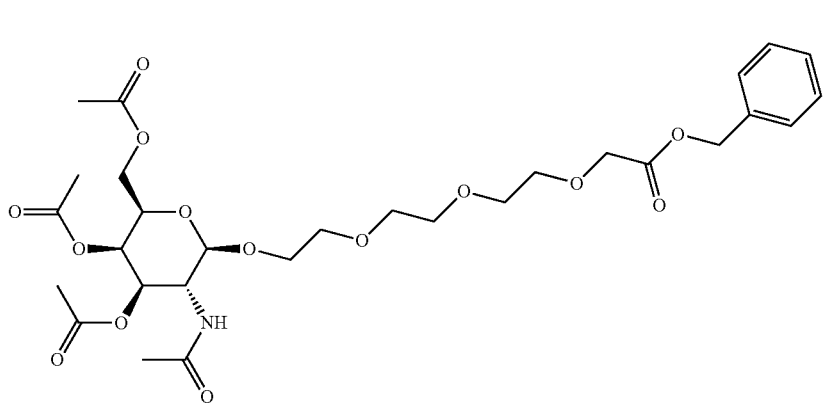

E. GalNAc Cluster Benzyl Ester

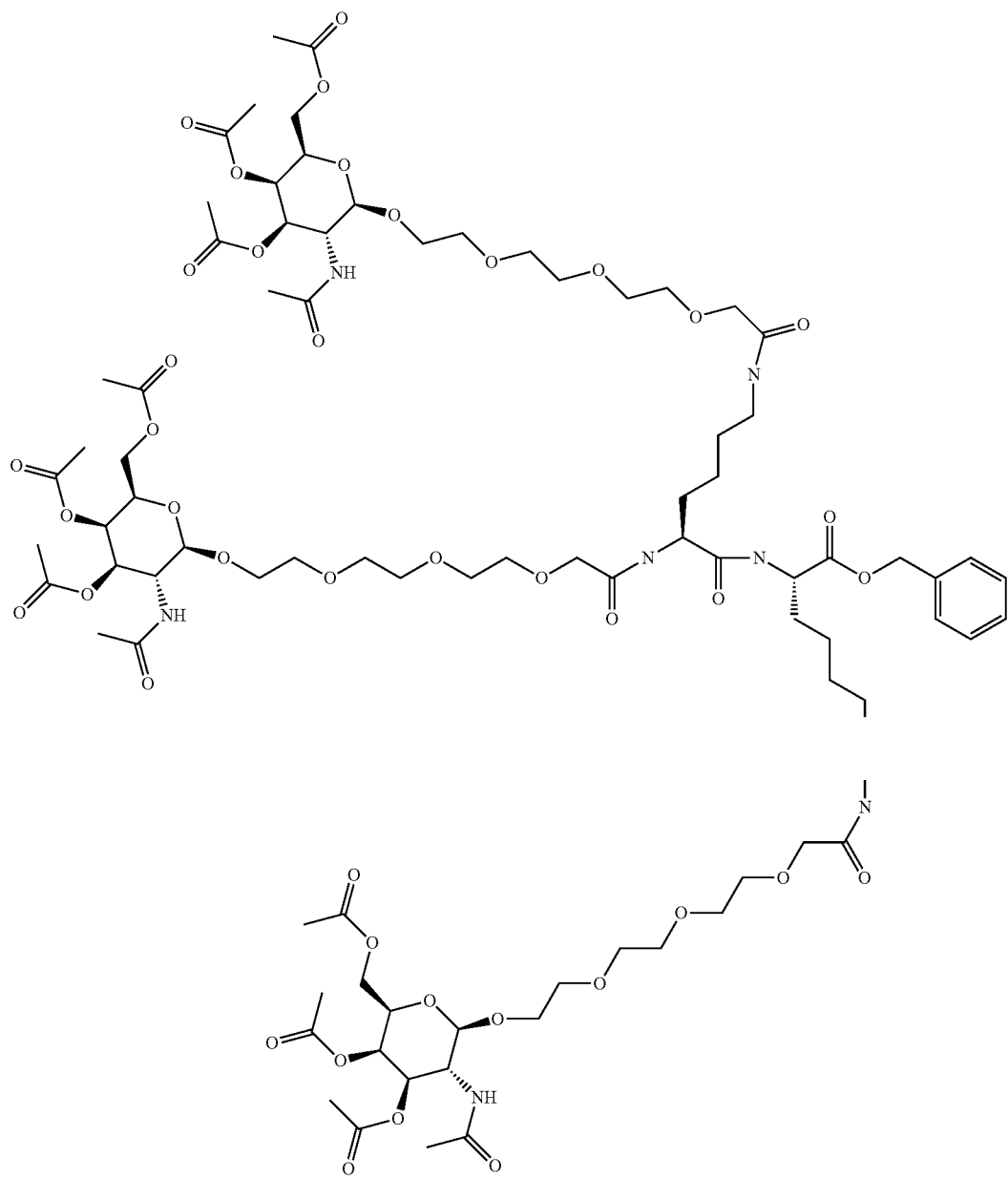

The above prepared (2-{2-[2-((2R,3R,4R,5R,6R)-4,5-diacetoxy-6-acetoxymethyl-3-acetylamino-tetrahydro-pyran-2-yloxy)-ethoxy]-ethoxy}-ethoxy)-acetic acid (2.820 g, 5.246 mmol) and (S)-6-amino-2-((S)-2,6-diamino-hexanoylamino)-hexanoic acid benzyl ester hydrochloride (preparation see below, 0.829 g, 1.749 mmol) were dissolved in a mixture of 32 mL of CH$_2$Cl$_2$ and 3.2 mL of DMF, treated successively with Hünig's base (2.096 ml, 12.25 mmol), 1-hydroxy-7-azabenzotriazole (0.714 g, 5.248 mmol) and 1-(3-dimethyl-aminopropyl)-3-ethylcarbodiimide hydrochloride (1.006 g, 5.248 mmol), and stirred over night at ambient temperature. All volatiles were removed i.V., and the crude reaction mixture purified by preparative HPLC (38 runs, Gemini, 5μ, C18) to give after lyophilization 1.650 g of the title product as white powder. MS (ISP): 1945.8 [M+Na]$^+$. NMR (600 MHz, DMSO).

F. GalNAc Cluster Free Acid (17S,20S)-1-((2R,3R,4R,5R,6R)-3-acetamido-4,5-diacetoxy-6-(acetoxymethyl)tetrahydro-2H-pyran-2-yloxy)-20-(1-((2R,3R,4R,5R,6R)-3-acetamido-4,5-diacetoxy-6-(acetoxymethyl)tetrahydro-2H-pyran-2-yloxy)-11-oxo-3,6,9-trioxa-12-azahexadecan-16-yl)-17-(2-(2-(2-(2-((2R,3R,4R,5R,6R)-3-acetamido-4,5-diacetoxy-6-(acetoxymethyl)tetrahydro-2H-pyran-2-yloxy)ethoxy)ethoxy)ethoxy)acetamido)-11,18-dioxo-3,6,9-trioxa-12,19-diazahenicosan-21-oic acid.

The above prepared GalNAc Cluster benzyl ester (0.674 g, 0.350 mmol) was dissolved in 50 mL of MeOH and hydrogenated over 0.065 g of Pd/C (10%) under 1 atm. of $H_2$ at ambient temperature for 4 h. Filtration over Celite and evaporation of the solvent left 0.620 g of the title compound as a white foam. MS (ISP): 1917.0 $[M+2H]^{2+}$. NMR (600 MHz, DMSO).

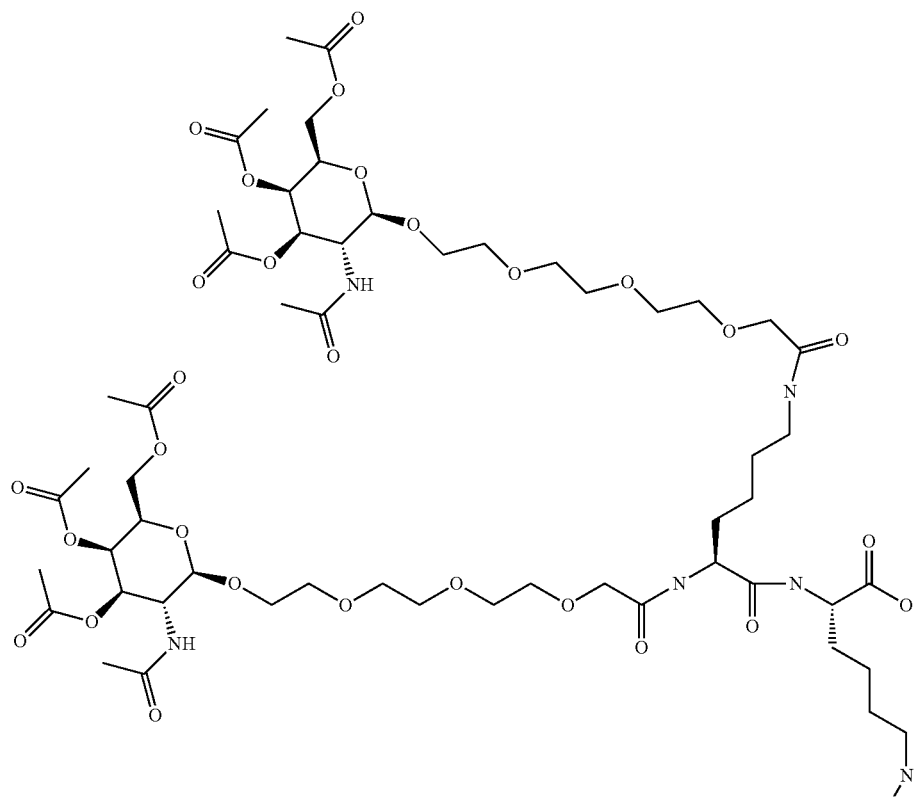

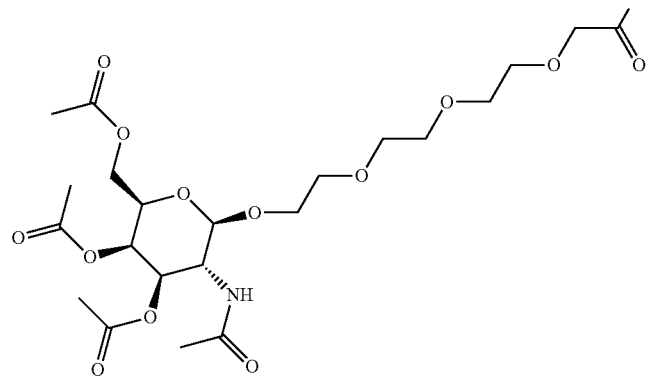

Example 14

(S)-6-amino-2-((S)-2,6-diamino-hexanoylamino)-hexanoic acid benzyl ester hydrochloride The building block (S)-6-amino-2-((S)-2,6-diamino-hexanoylamino)-hexanoic acid benzyl ester hydrochloride was synthesized as follows:

A. (S)-6-tert-Butoxycarbonylamino-2-(9H-fluoren-9-ylmethoxycarbonylamino)-hexanoic acid benzyl ester

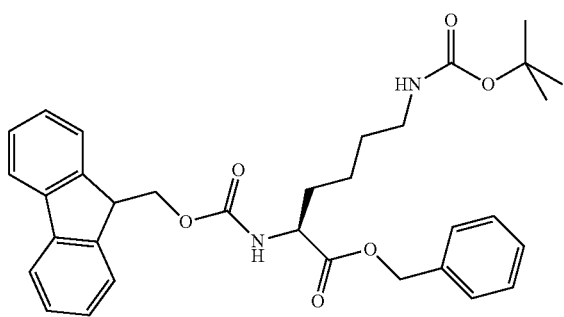 [SMILES: CC(C)(C)OC(=O)NCCCC[C@H](NC(=O)OCC1c2ccccc2-c2ccccc21)C(=O)OCc1ccccc1]

(S)-6-tert-Butoxycarbonylamino-2-(9H-fluoren-9-ylmethoxycarbonylamino)-hexanoic acid (5.00 g, 10.67 mmol) and phenyl-methanol (2.305 g, 21.34 mmol) were dissolved in 25 mL of $CH_2Cl_2$ and treated successively with N-hydroxybenzotriazole (1.933 g, 11.74 mmol), 1-ethyl-3-(3-dimethylaminopropyl)carbodiimide hydrochloride (EDC, 2.250 g, 11.74 mmol), and ethyl-diisopropyl-amine (2.137 ml, 12.49 mmol). After stirring for 90 min, the volatiles were removed i.V. at ambient temperature, the residue taken up in ethyl acetate, washed with water, $NH_4Cl$-solution and brine, dried over $Na_2SO_4$, and evaporated. The crude mixture was then dissolved in 20 mL of ethanol, and the product precipitated by adding 10 mL of water. Filtration and drying yielded 5.669 g of the title compound which was recrystallized from ethanol/hexane to give 4.27 g of pure benzyl ester. MS (ISP): 559.2 [M+H]$^+$.

B. (S)-2-((S)-2,6-Bis-tert-butoxycarbonylamino-hexanoylamino)-6-tert-butoxycarbonylamino-hexanoic acid benzyl ester

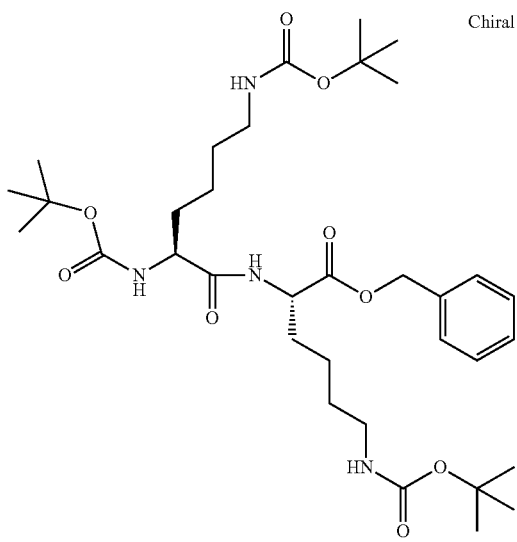 [SMILES: CC(C)(C)OC(=O)NCCCC[C@H](NC(=O)OC(C)(C)C)C(=O)N[C@@H](CCCCNC(=O)OC(C)(C)C)C(=O)OCc1ccccc1]

The above prepared (S)-6-tert-Butoxycarbonylamino-2-(9H-fluoren-9-ylmethoxy-carbonylamino)-hexanoic acid benzyl ester (4.270 g, 7.643 mmol) was dissolved in 15 mL of THF and treated with 15 mL of diethylamine. After 4 h at ambient temperature MS and TLC indicated the absence of starting material. Evaporation of the solvents and azeotropic drying with toluene afforded 4.02 g of the free amine which was used directly in the next step.

Commercially available (S)-2,6-bis-tert-butoxycarbonylamino-hexanoic acid (3.177 g, 9.17 mmol) was dissolved in 13 mL of $CH_2Cl_2$ and treated at 0° C. with ethyl-diisopropylamine (4.71 ml, 27.5 mmol), O-(1,2-dihydro-2-oxo-pyridyl)-1-1,1,3,3-tetramethyluronium tetrafluoroborate (TPTU, 2.725 g, 9.172 mmol) and, 15 min. later, with the above prepared amine as a solution in minimal $CH_2Cl_2$ and 1.57 mL of ethyl-diisopropyl-amine (1.2 eq.). The reaction was allowed to proceed for 2 h at ambient temperature. All volatiles were removed i.V., the residue taken up in ethyl acetate, washed with $NaHCO_3$-solution, $NH_4Cl$-solution and water, dried over $Na_2SO_4$, and evaporated. Flash chromatography ($SiO_2$, heptane/ethyl acetate=4/6) followed by crystallization from heptane/minimal amounts of ethyl acetate produced 4.516 g of the title compound as a white solid. MS (ISP): 665.4 [M+H]$^+$.

C. (S)-6-Amino-2-((S)-2,6-diamino-hexanoylamino)-hexanoic acid benzyl ester trihydrochloride

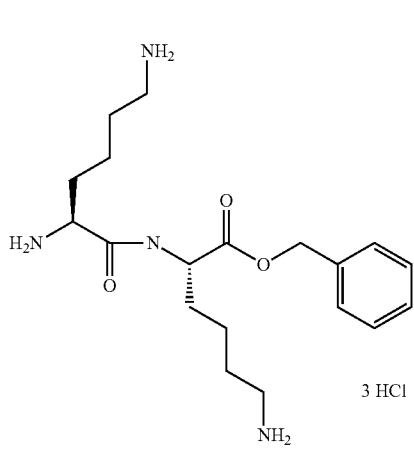

The above prepared (S)-2-((S)-2,6-bis-tert-butoxycarbonylamino-hexanoylamino)-6-tert-butoxycarbonylamino-hexanoic acid benzyl ester (4.516, 6.793 mmol) was dissolved in 4 mol/L HCl in dioxane. After a couple of minutes, gas evolved and a precipitate was formed. After 3 h at ambient temperature, the reaction mixture was carefully evaporated and scrupulously dried to yield 3.81 g of the title compound as an off-white foam which was used without further purification for Example 13. E. GalNAc Cluster benzyl ester above. MS (ISP): 365.3 [M+H]$^+$.

Example 15

GalNAc Cluster-siRNA Conjugates

A. Compound 1

(150 mg, 0.082 mmol) was dissolved in dry methanol (5.5 ml) and 42 μL sodium methylate were added (25% solution in MeOH). The mixture was stirred under an argon atmosphere for 2 h at RT. An equal amount of methanol was added as well as portions of an anionic exchange material Amberlite IR-120 to generate a pH around 7.0. The Amberlite was removed by filtration. The solution was dried with $Na_2SO_4$, and the solvent was removed under reduced pressure. Compound 2 was obtained in quantitative yield as a white foam. TLC (SiO$_2$, dichloromethane (DCM)/MeOH 5:1+0.1% CH$_3$COOH): R$_f$ 2=0.03; for detection a solution of sulfuric acid (5%) in MeOH was used followed by heating. ESI-MS, direct injection, negative mode; [M−H]$^{-1}$$_{calculated}$: 1452.7; [M−H]$^{1-}$$_{measured}$: 1452.5.

B. Compound 2

(20 mg, 0.014 mmol) was co-evaporated with pyridine and dichloromethane. The residue was dissolved in dry DMF (0.9 ml) and a solution of N-Hydroxysuccinimide (NHS) in DMF (1.6 mg, 0.014 mmol) was added while stirring under an argon atmosphere. At 0° C. a solution of N,N'-Dicyclohexylcarbodiimide (DCC) in DMF (3.2 mg, 0.016 mmol) was slowly added. The reaction was allowed to warm to RT and stirred over night. Compound 3 was used without further purification for conjugation to RNA.

C. Synthesis of Amino-Modified RNA.

RNA equipped with a C-6-amino linker at the 5'-end of the sense strand was produced by standard phosphoramidite chemistry on solid phase at a scale of 1215 µmol using an ÄKTA Oligopilot 100 (GE Healthcare, Freiburg, Germany) and controlled pore glass as solid support. RNA containing 2'-O-methyl nucleotides were generated employing the corresponding phosphoramidites, 2'-O-methyl phosphoramidites and TFA-hexylaminolinker amidite. Cleavage and deprotection as well as purification was achieved by methods known in the field (Wincott F., et al, NAR 1995, 23, 14, 2677-84).

The amino-modified RNA was characterized by anion exchange HPLC (purity: 96.1%) and identity was confirmed by ESI-MS ([M+H]$^{1+}$$_{calculated}$: 6937.4; [M+H]$^{1+}$$_{measured}$: 6939.0. Sequence: 5'-(NH$_2$C$_6$)GGAAUCuuAuAuuuGAUC-cAsA-3' (SEQ ID 1); u,c: 2'-O-methyl nucleotides of corresponding bases, s: phosphorothioate.

D. Conjugation of GalNAc Cluster to RNA.

Figure 6:
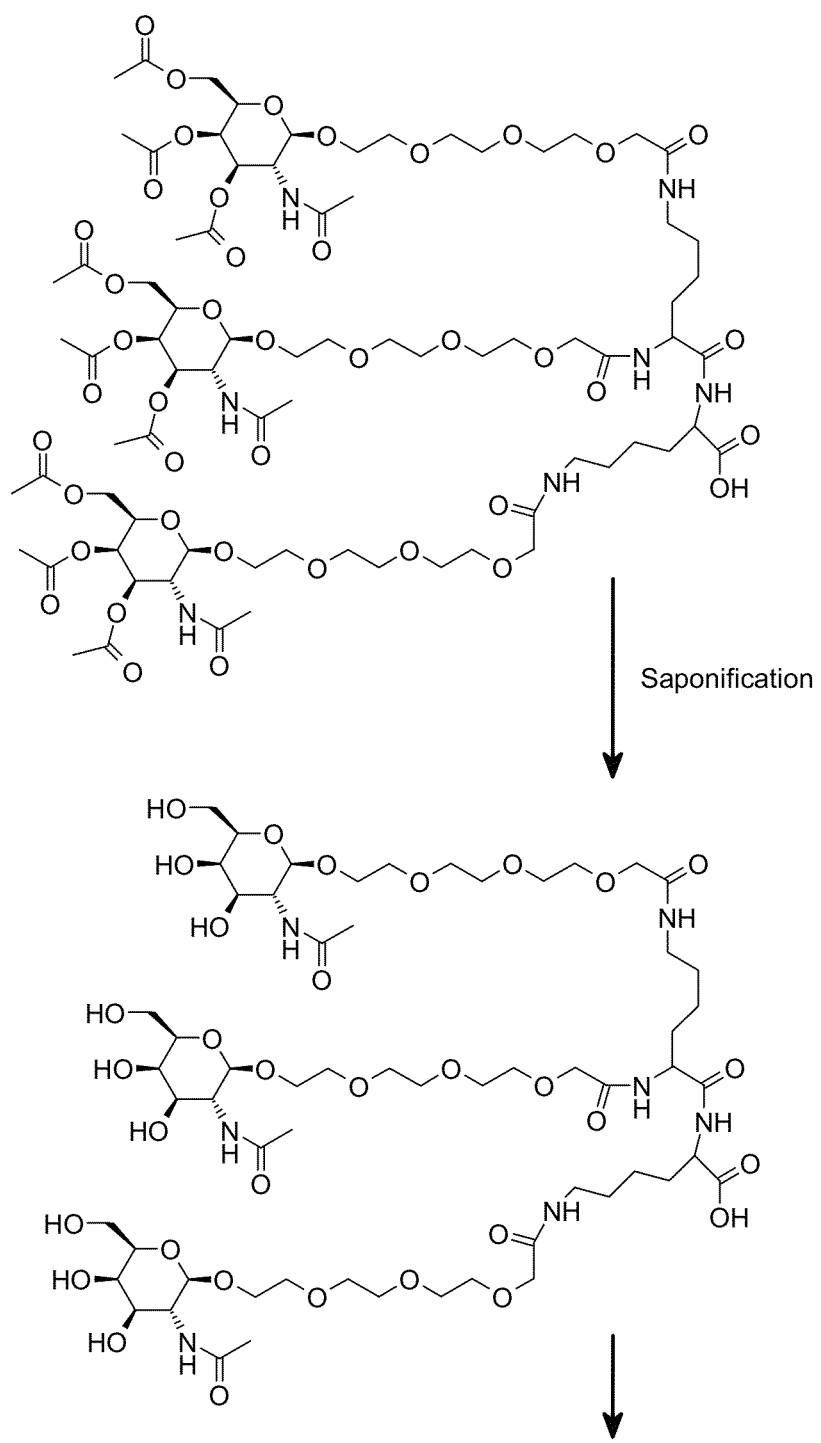
FIG. 6. Linkage of GalNAc Cluster to RNA
Figure 6:
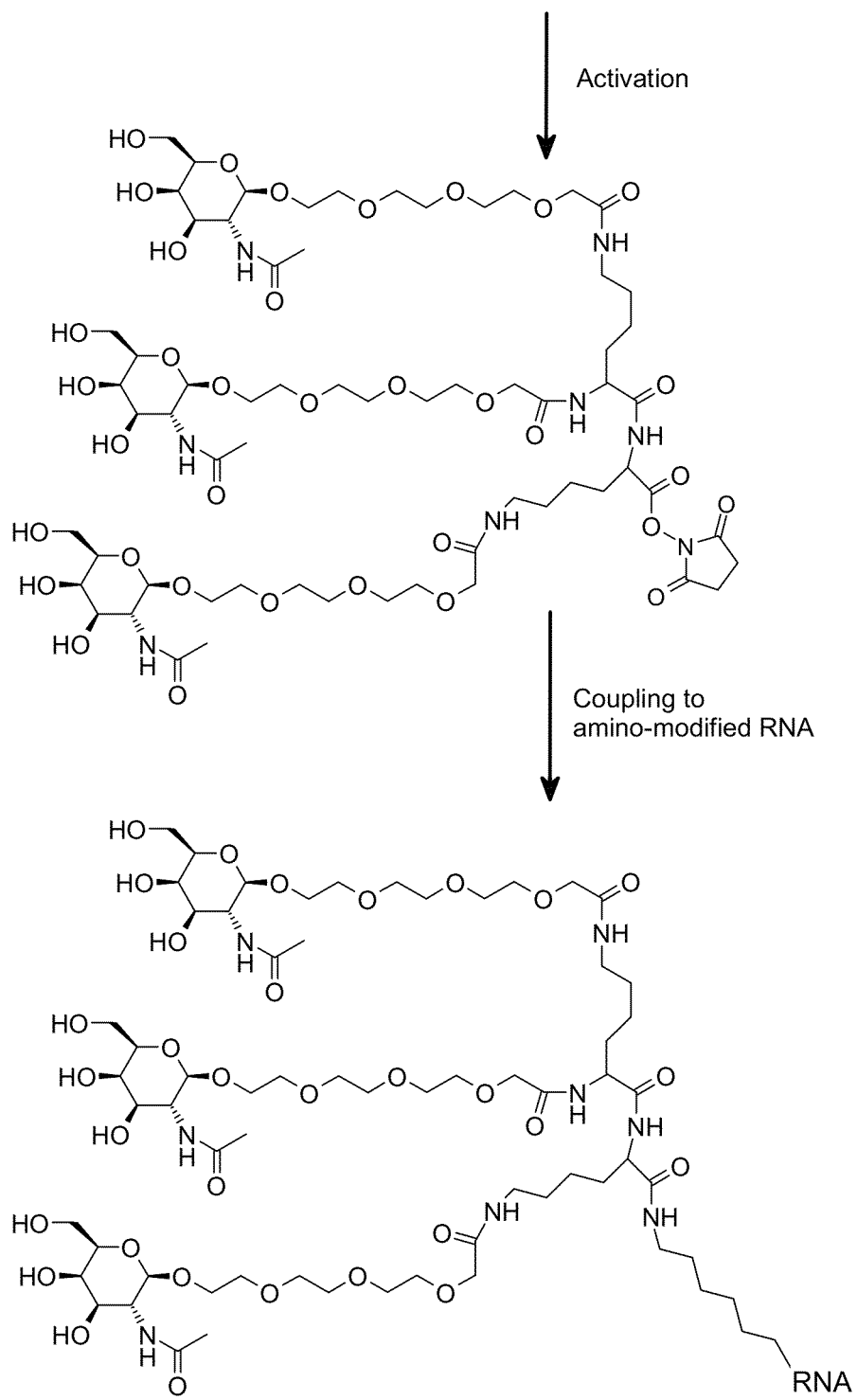

RNA (2.54 µmol) equipped with a C-6 amino linker at the 5'-end was lyophilized and dissolved in 250 µL sodium borate buffer (0.1 mol/L sodium borate, pH 8.5, 0.1 mol/L KCl) and 1.1 mL DMSO. After addition of 8 µL N,N-Diisopropylethylamine (DIPEA), a solution of compound 3 (theoretically 0.014 mmol) in DMF was slowly added under continuous stirring to the RNA solution. The reaction mixture was agitated at 35° C. overnight. The reaction was monitored using RP-HPLC (Resource RPC 3 ml, buffer: A: 100 mM Triethylammonium acetate (TEAA, 2.0 M, pH 7.0) in water, B: 100 mM TEAA in 95% acetonitrile, gradient: 5% B to 22% B in 20 CV). After precipitation of RNA using sodium acetate (3 M) in EtOH at −20° C., the RNA conjugate was purified using the conditions described above. The pure fractions were pooled, and the desired conjugate 4 was precipitated using sodium acetate/EtOH to give the pure RNA conjugate. Conjugate 4 has been isolated in 59% yield (1.50 µmol). The purity of conjugate 4 was analyzed by anion exchange HPLC (purity: 85.5%) and identity was confirmed by ESI-MS ([M+H]$^{1+}$$_{calculated}$: 8374.4; [M+H]$^{1+}$$_{measured}$: 8376.0. (FIG. 6.)

E. Conjugate 4 (Sense Strand) was Annealed with an 2'-O-Methyl-Modified Antisense Strand.

Sequence: 5'-uuGGAUcAAAuAuAAGAuUCcscsU-3' (SEQ ID 2). The siRNA conjugate directed against the apolipoprotein B mRNA was generated by mixing an equimolar solution of complementary strands in annealing buffer (20 mM sodium phosphate, pH 6.8; 100 mM sodium chloride), heated in a water bath at 85-90° C. for 3 min, and cooled to RT over a period of 3-4 h. Duplex formation was confirmed by native gel electrophoresis.

Example 16

Hydrophobic Group-siRNA Conjugates

SEQ ID 3:

(NHSC10)GGAUfCfAUfCfUfCfAAGUfCfUfUfACfdTsdT

(Amine)(COC9)GGAUfCfAUfCfUfCfAAGUfCfUfUfACfdTsdT

RNA synthesis was performed on solid phase by conventional phosphoramidite chemistry on an ÄKTA Oligopilot 100 (GE Healthcare, Freiburg, Germany) and controlled pore glass (CPG) as solid support.

The 5'-C10-NHS ester modified sense strand, (NHSC10) GGAUfCfAUfCfUfCfAAGUfCfUfUfACfdTsdT (SEQ ID 3) was prepared employing 5'-Carboxy-Modifier C10 amidite from Glen Research (Virginia, USA). The activated RNA, still attached to the solid support was used for conjugation with lipophilic amines listed in the table below. Cf and Uf are 2'-fluoronucleotides of the corresponding bases and s is a phosphorothioate linkage.

```
Sense strand sequence:
                                             (SEQ ID 3)
5'-(COC9)GGAUfCfAUfCfUfCfAAGUfCfUfUfACfdTsdT-3'

Antisense strand sequence:
                                             (SEQ ID 4)
5'-GUfAAGACfUfUfGAGAUfGAUfCfCfdTsdT-3'
```

100 mg of the sense strand CPG (loading 60 µmol/g, 0.6 µmol RNA) were mixed with 0.25 mmol of the corresponding amine obtained from, Sigma Aldrich Chemie GmbH (Taufkirchen, Germany) or Fluka (Sigma-Aldrich, Buchs, Switzerland).

TABLE 16

Lipophilic amines used in forming hydrophobic group-siRNA conjugates

| Nr | Lipophilic Amine | mg | mmol | ml solvent |
|---|---|---|---|---|
| 2 | N-Hexylamine | 25 | 0.25 | 1 mL CH$_2$Cl$_2$ |
| 3 | Dodecylamine | 50 | 0.25 | 0.55 mL CH$_3$CN, 0.45 mL CH$_2$Cl$_2$ |
| 4 | Octadecylamine | 67 | 0.25 | 1 mL CH$_2$Cl$_2$ |
| 5 | Didecylamine | 74 | 0.25 | 1 mL CH$_2$Cl$_2$ |
| 6 | Didodecylamine | 88 | 0.25 | 1 mL CH$_2$Cl$_2$ |
| 7 | Dioctadecylamine | 67 | 0.12 | 0.45 mL CH$_2$Cl$_2$, 0.45 mL Cyclohexane |

The mixture was shaken for 18 h at 40° C. The RNA was cleaved from the solid support and deprotected with an aqueous ammonium hydroxide solution (NH$_3$, 33%) at 45° C. overnight. The 2'-protecting group was removed with TEAx3HF at 65° C. for 3.5 h. The crude oligoribonucleotides were purified by RP-HPLC (Resource RPC 3 ml, buffer: A: 100 mM TEAA in water, B: 100 mM TEAA in 95% $CH_3CN$, gradient: 3% B to 70% B in 15 CV, except for Nr 7: gradient from 3% B to 100% B in 15 CV).

TABLE 17

Hydrophobic group-RNA conjugates, characterized by RP- HPLC and ESI-MS (negative mode).

| Nr | Purity RP-HPLC % | ESI-MS [M − H] calculated | ESI-MS [M − H] found |
|---|---|---|---|
| 2 | 90 | 6963.4 | 6963.0 |
| 3 | 99 | 7047.4 | 7047.2 |
| 4 | 98 | 7131.5 | 7131.4 |
| 5 | 99 | 7159.6 | 7159.3 |

TABLE 17-continued

Hydrophobic group-RNA conjugates, characterized by RP- HPLC and ESI-MS (negative mode).

| Nr | Purity RP-HPLC % | ESI-MS [M − H] calculated | ESI-MS [M − H] found |
|---|---|---|---|
| 6 | 99 | 7215.7 | 7215.0 |
| 7 | 98 | 7384.0 | 7383.2 |

To generate siRNA from RNA single strand, equimolar amounts of complementary sense and antisense strands were mixed in annealing buffer (20 mM sodium phosphate, pH 6.8; 100 mM sodium chloride), heated at 80° C. for 3 min, and cooled to RT over a period of 3-4 h. The siRNA, which are directed against factor VII mRNA were characterized by gel electrophoresis.

The invention claimed is:

1. A conjugate delivery system for delivering an RNA interference polynucleotide to a liver cell in vivo comprising:

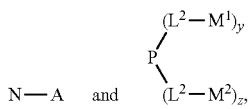

wherein,

P is a membrane active polyamine $L^2$ is a disubstituted maleamate linkage, $M^1$ is a charge neutral masking agent containing a galactose derivative having affinity for the asialoglycoprotein receptor, $M^2$ is a charge neutral masking agent containing a polyethylene glycol, y is an integer greater than or equal to 1, z is an integer greater than or equal to zero, the value y+z is greater than 50% of amines on P, N is an RNA interference polynucleotide, A comprises a galactose trimer, positive charge of P is neutralized and membrane activity of P is reversibly inhibited by modification of greater than 50% of P amines by attachment of $M^1$ and $M^2$ through the physiologically pH-labile maleamate linkage linkages $L^2$, and cleavage of $L^2$ restores amines and membrane activity of P.

2. The composition of claim 1 wherein the RNA interference polynucleotide is selected from the group consisting of: DNA, RNA, dsRNA, siRNA, and miRNA.

3. The composition of claim 1 wherein the liver cell consists of a hepatocyte.

4. The composition of claim 1 wherein the reversibly masked membrane active polyamine is soluble in water.

5. The composition of claim 4 wherein the membrane active polyamine comprises an amphipathic random copolymer.

6. The composition of claim 4 wherein the membrane active polyamine contains two or more different monomers.

7. The composition of claim 6 wherein the membrane active polyamine contains three or more different monomers.

8. The composition of claim 7 wherein the membrane active polymer is composed of amine-containing monomers, lower hydrophobic group monomers, and higher hydrophobic group monomers.

9. The composition of claim 5 wherein the random copolymer is selected from the group consisting of poly(vinyl ether) and poly(acrylate).

10. The composition of claim 8 wherein the amine-containing monomers, lower hydrophobic group monomers, and higher hydrophobic group monomers are present in a ratio of 4-8 amine-containing monomers:3-5 lower hydrophobic group monomers:1 higher hydrophobic group monomers.

11. The composition of claim 1 wherein the masking agents are reversibly linked to at least 70% of the amines on the polyamine.

12. The composition of claim 11 wherein the masking agents are reversibly linked to at least 80% of the amines on the polyamine.

13. The composition of claim 1 wherein the reversibly modified polymer has a zeta potential between 0 and −20 mV at pH 8.

14. The composition of claim 13 wherein the reversibly modified polymer has a zeta potential between 0 and −10 mV at pH 8.

15. The composition of claim 1 wherein the composition is provided in a pharmaceutically acceptable carrier or diluent.

16. The composition of claim 1 wherein N is linked to A via a physiologically labile linkage $L^1$.

17. The composition of claim 16 wherein $L^1$ is a physiologically labile covalent linkage that is orthogonal to $L^2$.

18. The composition of claim 1 wherein the ratio of galactose derivative to PEG linked to the polymer is 1 to 0.5-2.

19. The composition of claim 1 wherein the galactose derivative consists of an N-acetylgalactosamine.

20. The composition of claim 1 wherein the galactose trimer consists of an N-acetylgalactosamine trimer.

21. A composition for delivering an oligonucleotide to a liver cell in vivo comprising:
   a) an oligonucleotide covalently linked to a galactose trimer; and,
   b) a reversibly masked and targeted amphipathic polymer comprising a terpolymer synthesized from amine-containing monomers, lower hydrophobic group-containing monomers, and higher hydrophobic group-containing monomers to which a plurality of galactose derivatives and PEG groups are individually linked to said polymer via pH labile disubstituted maleamic bonds and wherein cleavage of said pH labile disubstituted maleamic bonds yields amine groups thereby generating a membrane active polyamine.

22. A method of manufacturing an RNA oligonucleotide delivery composition comprising:
   a) forming a membrane active polyamine;
   b) forming a first masking agent comprising a charge neutral disubstituted maleic anhydride containing a galactose derivative;
   c) forming a second masking agent comprising a charge neutral disubstituted maleic anhydride containing a polyethylene glycol;
   d) reversibly inhibiting membrane activity of the membrane active polyamine wherein the inhibiting consists of modifying 50% or more of the amines on the polyamine by reacting the polyamine with the first and second masking agents thereby linking a plurality of galactose derivatives and a plurality of polyethylene glycols to the membrane active polymer via physiologically pH-labile disubstituted maleamate linkages; and,
   e) linking the RNA interference polynucleotide to a galactose trimer;
   f) providing the RNA interference polynucleotide and the reversibly inhibited membrane active polyamine in solution suitable for administration in vivo.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: sense strand of siRNA targeting Mus musculus
      apoB
<220> FEATURE:
<221> NAME/KEY: modified_base
<222> LOCATION: 21
<223> OTHER INFORMATION: 5'-phosphorothioate adenosine
<220> FEATURE:
<221> NAME/KEY: modified_base
<222> LOCATION: 7, 8, 10, 12, 13, 14, 19
<223> OTHER INFORMATION: 2'-O-methyl corresponding nucleoside

<400> SEQUENCE: 1
ggaaucuuau auuugaucca a                                              21

<210> SEQ ID NO 2
<211> LENGTH: 23
<212> TYPE: RNA
<213> ORGANISM: Artificial Sequence
<220> FEATURE:
<223> OTHER INFORMATION: antisense strand of siRNA targeting Mus
      musculus apoB
<220> FEATURE:
<221> NAME/KEY: modified_base
<222> LOCATION: 22
<223> OTHER INFORMATION: 5'-phosphorothioate cytidine
<220> FEATURE:
<221> NAME/KEY: modified_base
<222> LOCATION: 23
<223> OTHER INFORMATION: 5'-phosphorothioate uridine
<220> FEATURE:
<221> NAME/KEY: modified_base
<222> LOCATION: 1, 2, 7, 11, 13, 18, 21, 22
<223> OTHER INFORMATION: 2'-O-methyl corresponding nucleoside

<400> SEQUENCE: 2
uuggaucaaa uauaagauuc ccu                                            23

<210> SEQ ID NO 3
<211> LENGTH: 21
<212> TYPE: DNA
<213> ORGANISM: Artificial Sequence
<220> FEATURE:
<223> OTHER INFORMATION: sense strand of siRNA targeting Mus musculus
      FVII
```

```
<220> FEATURE:
<221> NAME/KEY: modified_base
<222> LOCATION: 1, 2, 3, 6, 11, 12, 13, 18
<223> OTHER INFORMATION: 2'-hydroxy corresponding nucleoside
<220> FEATURE:
<221> NAME/KEY: modified_base
<222> LOCATION: 4, 5, 7, 8, 9, 10, 14, 15, 16, 17, 19
<223> OTHER INFORMATION: 2'-deoxy-2'-fluoro corresponding nucleoside

<400> SEQUENCE: 3
ggaucaucuc aagucuuact t                                              21

<210> SEQ ID NO 4
<211> LENGTH: 21
<212> TYPE: DNA
<213> ORGANISM: Artificial Sequence
<220> FEATURE:
<223> OTHER INFORMATION: antisense strand of siRNA targeting Mus
      musculus FVII
<220> FEATURE:
<221> NAME/KEY: modified_base
<222> LOCATION: 1, 3, 4, 5, 6, 10, 11, 12, 13, 15, 16
<223> OTHER INFORMATION: 2'-hydroxy corresponding nucleoside
<220> FEATURE:
<221> NAME/KEY: modified_base
<222> LOCATION: 2, 7, 8, 9, 14, 17, 18, 19
<223> OTHER INFORMATION: 2'-deoxy-2'-fluoro corresponding nucleoside
<220> FEATURE:
<221> NAME/KEY: modified_base
<222> LOCATION: 21
<223> OTHER INFORMATION: 5'-phosphorothioate thymidine

<400> SEQUENCE: 4
guaagacuug agaugaucct t                                              21
```